United States Patent
Fagerlund et al.

(10) Patent No.: US 11,365,238 B2
(45) Date of Patent: Jun. 21, 2022

(54) SEQUENCING CHICKEN ANTIBODY REPERTOIRES FOLLOWING HYPERIMMUNIZATION AND THE IDENTIFICATION OF ANTIGEN-SPECIFIC MONOCLONAL ANTIBODIES

(71) Applicant: Camas Incorporated, Le Center, MN (US)

(72) Inventors: Jeff Fagerlund, Lakeville, MN (US); Bradley M. Mitteness, Ghent, MN (US); Connie Phillips, Ankeny, IA (US)

(73) Assignee: CAMAS INCORPORATED, Le Center, MN (US)

( * ) Notice: Subject to any disclaimer, the term of this patent is extended or adjusted under 35 U.S.C. 154(b) by 401 days.

(21) Appl. No.: 16/060,304

(22) PCT Filed: Dec. 7, 2016

(86) PCT No.: PCT/US2016/065331
§ 371 (c)(1),
(2) Date: Jun. 7, 2018

(87) PCT Pub. No.: WO2017/100289
PCT Pub. Date: Jun. 15, 2017

(65) Prior Publication Data
US 2020/0407426 A1    Dec. 31, 2020

Related U.S. Application Data

(60) Provisional application No. 62/264,090, filed on Dec. 7, 2015.

(51) Int. Cl.
*C07K 16/00* (2006.01)
*C07K 16/12* (2006.01)

(52) U.S. Cl.
CPC .......... *C07K 16/00* (2013.01); *C07K 16/1242* (2013.01); *C07K 2317/23* (2013.01); *C07K 2317/622* (2013.01)

(58) Field of Classification Search
CPC combination set(s) only.
See application file for complete search history.

(56) References Cited

U.S. PATENT DOCUMENTS

| | | | | |
|---|---|---|---|---|
| 2007/0141049 A1* | 6/2007 | Bredehorst | .......... | C07K 16/462 424/133.1 |
| 2007/0258978 A1 | 11/2007 | Loibner et al. | | |
| 2008/0075712 A1* | 3/2008 | Hattori | .......... | A61P 37/00 424/130.1 |
| 2010/0196375 A1* | 8/2010 | Kaushik | .......... | A61P 31/12 424/135.1 |

FOREIGN PATENT DOCUMENTS

| WO | 2010037402 A1 | 4/2010 |
|---|---|---|
| WO | 2012006437 A2 | 1/2012 |

OTHER PUBLICATIONS

Sarker et al. "Randomized, placebo-controlled, clinical trial of hyperimmunized chicken egg yolk immunoglobulin in children with rotavirus diarrhea" J. Pediatric Gastroenterology and Nutrition, 32: 19-25, 2001 (Year: 2001).*
Galson et al. "Analysis of B cell repertoire dynamics following Hepatitis B vaccination in humans, and enrichment of vaccine-specific antibody sequences" EBioMedicine 2 (2015) 207-2079 (Year: 2015).*
Smith et al. "Rapid generation of fully human monoclonal antibodies specific to a vaccinating antigen" Nat Protoc. 2009: 4(3): 372-384 (2009) (Year: 2009).*
Swinkels et al. "Vaccination induced antibodies to recombinant avian influenza A virus M2 protein or synthetic M2e peptide do not bind to the M2 protein on the virus or virus infected cells" Virology Journal 2013, 10: 206, pp. 1-8 (Year: 2013).*
Arakawa, "Immunoglobulin gene hyperconversion ongoing in chicken splenic germinal centers" EMBO Journal, 15(10), 1996, pp. 2540-2546 (Year: 1996).*
Poulsen et al. "Limits for antibody affinity maturation and repertoire diversificaiton in hypervaccinated humans" J Immunol 2011, 187: 4229-4235. (Year: 2011).*
Jiang, Z. et al. "Isolation of RNA from equine peripheral blood cells: comparison methods" SpringerPlus 2013, 2:478; DOI 10.1186/2193-1801-2-478, p. 1-6.
Rice J.A. et al. "Mannheimia haemolytica and bovine respiratory disease" Animal Health Research Reviews, 2008, 8 (2), 117-128.
Search Report issued for International Patent Application No. PCT/US2016/065331 dated Jun. 1, 2017.
Written Opinion of the International Searching Authority issued for International Patent Application No. PCT/US2016/065331 dated Jun. 1, 2017.
Abdelmagid O. et al. "Fine Mapping of Bovine Herpesvirus-1 (BHV-1) Glycoprotein D (gD) Neutralizing Epitopes by Type-Specific Monoclonal Antibodies and Sequence Comparison with BHV-5 gD." (1995) Virology. 206; 242-253.

(Continued)

*Primary Examiner* — Daniel E Kolker
*Assistant Examiner* — James L Rogers
(74) *Attorney, Agent, or Firm* — Westman, Champlin & Koehler, P.A.; Z. Peter Sawicki; Visala C. Goswitz

(57) ABSTRACT

Neutralizing antibodies through recombinant protein expression were identified by mining antibody repertoires by high-throughput second generation sequencing. Sequencing across the majority of light and heavy chain variable regions of chicken immunoglobulins was performed at two immunological time points: a non-immune (naive) state and a post-hyperimmunization state. The mRNA was extracted from unsorted and unselected PBMC populations and identification of antigen-specific antibody sequences leveraged the significant disparity of abundance of an individual B cell clone in non-immune and immunized states. Through bioinformatic analysis, candidate amino acid sequences for variable heavy chain and light chains were identified. Recombinant polypeptides with the binding domains having the identified amino acid sequences for variable heavy chain and light chains were expressed and screened using immunoassays to confirm antigen-specificity.

19 Claims, 7 Drawing Sheets

Specification includes a Sequence Listing.

(56) References Cited

OTHER PUBLICATIONS

Ayalew, S. et al. "Immunogenicity of Mannheimia haemolytica Recombinant Outer Membrane Proteins Serotype 1-Specific Antigen, OmpA, OmpP2, and OmpD15." (2011) Clinical Vaccine Immunology. 18(12): 2067-2074.
Carlson, L.M. et al. "Templated Insertions in the Rearranged Chicken IgL V Gene Segment Arise by Intrachromosomal Gene Conversion." (1990) Genes & Development. 4; 536-547.
Cheung, W.C. et al. "A Proteomics Approach for the Identification and Cloning of Monoclonal Antibodies from Serum." (2012) Nature Biotechnology. 30(5); 447-452.
Connolly, S.A. et al. "Glycoprotein D Homologs in Herpes Simplex Virus Type 1, Pseudorabies Virus, and Bovine Herpes Virus Type 1 Bind Directly to Human HveC (Nectin-1) with Different Affinities." (2001) Virology. 280; 7-18.
Dargatz, D.A. and Lombard, J.E. "Summary of BRD Data from the 2011 NAHMS Feedlot and Dairy Heifer Studies." (2014) Animal Health Research Reviews. 15(2); 123-125.
De Castro, E. et al. "ScanProsite: Detection of PROSITE Signature Matches and ProRule-associated Functional and Structural Residues in Proteins." (2006) Nucleic Acids Res. 1;34(Web Server issue):W362-5.
Engler, M. et al. "The Impact of Bovine Respiratory Disease: the Current Feedlot Experience." (2014) Animal Health Research Reviews. 15(2); 126-129.
Glanville, J. et al. "Naïve Antibody Gene-segment Frequencies are Heritable and Unaltered by Chronic Lymphocyte Ablation." (2011) Proceedings of the National Academy of Sciences of the United States of America. 108(50); 20066-20071.
Grant, J.A. et al. "Partial Amino Acid Sequences of Chicken and Turkey Immunoglobulin Light Chains. Homology with Mammalian Lambda Chains." (1971) Biochemistry. 10(16); 3123-3132.
Greiff, V. et al. "Quantitative Assessment of the Robustness of Next-Generation Sequencing of Antibody Variable Gene Repertoires from Immunized Mice." (2014) BMC Immunology. 15(40); doi: 10.1186/s12865-014-0040-5.
Hibi, T. and Dosch, H.M. "Limiting Dilution Analysis of the B Cell Compartment in Human Bone Marrow." European Journal of Immunology. (1986) 16; 139-145.
Hilton, M.W. "BRD in 2014: Where Have We Been, Where Are We Now, and Where Do We Want to Go?" (2014) Animal Health Research Reviews. 15(2); 120-122.
Hoet, R.M. et al. "Generation of High-affinity Human Antibodies by Combining Donor-derived and Synthetic Complementarity-determining-region Diversity." (2005) Nature Biotechnology. 23(3); 344-348.
Huang, Y. et al. "CD-HIT Suite: a Web Server for Clustering and Comparing Biological Sequences." (2010) Bioinformatics. 26(5); 680-682.
Lee, C.V. et al. "High-affinity Human Antibodies from Phage-displayed Synthetic Fab Libraries with a Single Framework Scaffold. " (2004) Journal of Molecular Biology. 340; 1073-1093.
Li, W. et al."Clustering of Highly Homologous Sequences to Reduce the Size of Large Protein Database." (2001) Bioinformatics. 17(3); 282-283.
Nash, D. et al. "Efficacy of an Intranasal Delivery of an Avian-derived Antibody Preparation Against Respiratory Pathogens in Prevention of Morbidity and Mortality of Newly Received Feedlot Cattle." (2007) Proceedings of the Fortieth Annual Conference, American Association of Bovine Practices. 277.
Nishibori, N. et al. "Humanization of Chicken Monoclonal Antibody Using a Phage-display System." (2006) Molecular Immunology. 43; 634-642.
Owen, J.A. et al. "Kuby Immunology. 7th edition." (2013) New York. WH Freeman and Company.
Parameswaran P. et al. "Convergent Antibody Signatures in Human Dengue." (2013) Cell Host & Microbe. 13, 691-700.
Ratcliffe, M.J.H. "Antibodies, Immunoglobulin Genes and the Bursa of Fabricius in Chicken B Cell Development." (2006) Developmental and Comparative Immunology. 30; 101-118.
Reddy, S.T. et al. "Monoclonal Antibodies Isolated without Screening by Analyzing the Variable-gene Repertoire of Plasma Cells." (2010) Nature Biotechnology. 28(9); 965-969.
Reynaud, C.A. et al. "A Hyperconversion Mechanism Generates the Chicken Preimmune Light Chain Repertoire." (1987) Cell. 48; 379-388.
Reynaud, C.A. et al. "Somatic Hyperconversion Diversifies the Single VH Gene of the Chicken with a High Incidence in the D Region." (1989) Cell. 59; 171-183.
Reynaud, C.A. et al. "The Chicken D Locus and its Contribution to the Immunoglobulin Heavy Chain Repertoire." (1991) European Journal of Immunology. 11; 2661-2670.
Schat, K.A. et al. "Avian Immunology. 2nd Edition." (2012) 109.
Sidhu, S.S. et al. "Phage-displayed Antibody Libraries of Synthetic Heavy Chain Complementarity Determining Regions." (2004) Journal of Molecular Biology. 338; 299-310.
Sievers, F. et al. "Fast, Scalable Generation of High-Quality Protein Multiple Sequence Alignments using Clustal Omega." (2011) Molecular Systems Biology. 11 (7); 539-544.
Thompson, C.B. and Neiman, P.E. "Somatic Diversification of the Chicken Immunoglobulin Light Chain Gene is Limited to the Rearranged Variable Region Gene Segment." (1987) Cell. 48; 369-378.
Tsurushita, N. et al. "Humanization of a Chicken anti-IL-12 Monoclonal Antibody." (2004) Journal of Immunological Methods. 295; 9-19.
USDA. "Feedlot 2011 Part I: Management Practices on U.S. Feedlots with a Capacity of 1,000 or More Head." (2013) USDA-APHIS-VS-CEAH-NAHMS. Fort Collins, CO. #626.0313.
Van Drunen Littel-van den Hurk S. et al. "Epitope Specificity of the Protective Immune Response Induced by Individual Bovine Herpesvirus-1 Glycoproteins." (1990) Vaccine. 8; 358-368.
Wu, L. et al. "Fundamental Characteristics of the Immunoglobulin VH Repertoire of Chickens in Comparison with Those of Humans, Mice, and Camelids." (2011) The Journal of Immunology. 188; 322-333.
Young, A.E. and Woolums, A.R. "Proceedings of the Bovine Respiratory Disease Symposium 2014: New Approaches to Bovine Respiratory Disease Prevention, Management, and Diagnosis." (2014) Animal Health Research Reviews. 15 (2); 119.
Molekulyarnaya boilogiya, Structura I biosintez nukleinovych kislot. M. "Vysshaya shkola", p. 14-21, 44-51, 308-317, with English Machine Translation.

\* cited by examiner

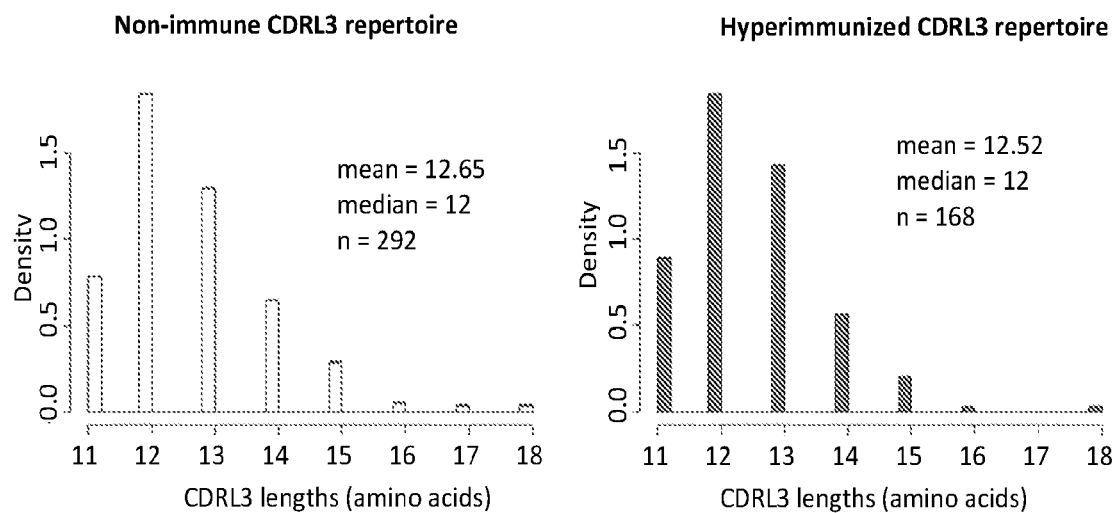
FIG. 5A  FIG. 5B
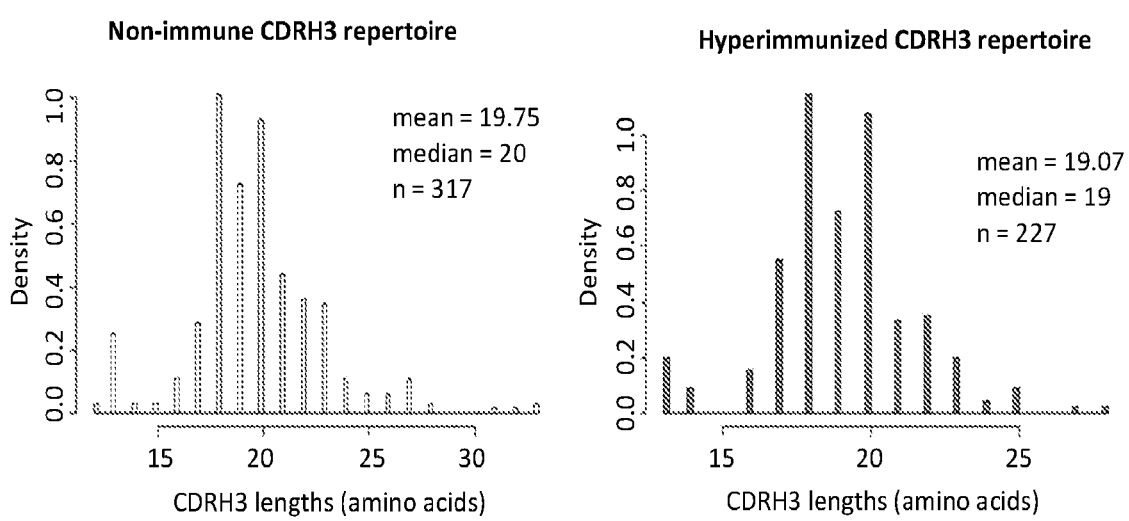
FIG. 5C  FIG. 5D ial Patent Application Ser. No. 62/264,090 has been referenced in the cross-reference section.

SEQUENCE LISTING

<160> NUMBER OF SEQ ID NOS: 35

<210> SEQ ID NO 1
<211> LENGTH: 22
<212> TYPE: DNA
<213> ORGANISM: Artificial Sequence
<220> FEATURE:
<223> OTHER INFORMATION: A synthetic primer

<400> SEQUENCE: 1
aaccgtcaag atcacctgct cc                                           22

<210> SEQ ID NO 2
<211> LENGTH: 18
<212> TYPE: DNA
<213> ORGANISM: Artificial Sequence
<220> FEATURE:
<223> OTHER INFORMATION: A synthetic primer

<400> SEQUENCE: 2
ggttgtcccg gccccaaa                                                18

<210> SEQ ID NO 3
<211> LENGTH: 19
<212> TYPE: DNA
<213> ORGANISM: Artificial Sequence
<220> FEATURE:
<223> OTHER INFORMATION: A synthetic primer

<400> SEQUENCE: 3
tctgcaaggc ctccgggtt                                               19

```
<210> SEQ ID NO 4
<211> LENGTH: 18
<212> TYPE: DNA
<213> ORGANISM: Artificial Sequence
<220> FEATURE:
<223> OTHER INFORMATION: A synthetic primer

<400> SEQUENCE: 4
ttcggtcccg tggcccca                                                   18

<210> SEQ ID NO 5
<211> LENGTH: 18
<212> TYPE: PRT
<213> ORGANISM: Gallus gallus

<400> SEQUENCE: 5

Cys Ala Lys Ser Ala Asn Ser Gly Asn Pro Asp Ala Gly Glu Ile Asp
1               5                  10                  15

Ala Trp

<210> SEQ ID NO 6
<211> LENGTH: 20
<212> TYPE: PRT
<213> ORGANISM: Gallus gallus

<400> SEQUENCE: 6

Cys Ala Lys Asn Ser Phe Ser Ser Gly Tyr Gly Trp Ser Ala Gly Thr
1               5                  10                  15

Ile Asp Ala Trp
            20

<210> SEQ ID NO 7
<211> LENGTH: 18
<212> TYPE: PRT
<213> ORGANISM: Gallus gallus

<400> SEQUENCE: 7

Cys Thr Arg Ser Ser Cys Gly Gly Asp His Glu Ser Gly Cys Ile Asp
1               5                  10                  15

Ala Trp

<210> SEQ ID NO 8
<211> LENGTH: 13
<212> TYPE: PRT
<213> ORGANISM: Gallus gallus

<400> SEQUENCE: 8

Cys Ala Arg Gly Gly Ala Gly His Asp Ile Asp Arg Trp
1               5                  10

<210> SEQ ID NO 9
<211> LENGTH: 24
<212> TYPE: PRT
<213> ORGANISM: Gallus gallus

<400> SEQUENCE: 9

Cys Ala Lys Thr Tyr Arg Gly Gly Tyr Cys Asp Asn Gly Asp Pro Cys
1               5                  10                  15

Ile Gly Tyr Arg Ile Gly Ala Trp
            20

<210> SEQ ID NO 10
```

-continued

```
<211> LENGTH: 18
<212> TYPE: PRT
<213> ORGANISM: Gallus gallus

<400> SEQUENCE: 10

Cys Val Lys Ser Asp Asp Gly Val Cys Cys Asp Ala Tyr Gly Ile Asp
1               5                   10                  15

Ala Trp

<210> SEQ ID NO 11
<211> LENGTH: 19
<212> TYPE: PRT
<213> ORGANISM: Gallus gallus

<400> SEQUENCE: 11

Cys Ala Lys Gly Pro Ser Gly Tyr Arg Tyr Leu Val Gly Asn Asn Ile
1               5                   10                  15

Asp Ala Trp

<210> SEQ ID NO 12
<211> LENGTH: 18
<212> TYPE: PRT
<213> ORGANISM: Gallus gallus

<400> SEQUENCE: 12

Cys Thr Arg Ser Ser Cys Gly Gly Asp His Glu Ala Gly Cys Ile Asp
1               5                   10                  15

Ala Trp

<210> SEQ ID NO 13
<211> LENGTH: 18
<212> TYPE: PRT
<213> ORGANISM: Gallus gallus

<400> SEQUENCE: 13

Cys Ala Lys Ser Ala Ala Gly Trp Cys Ala Asp Ala Gly Ile Ile Asp
1               5                   10                  15

Ala Trp

<210> SEQ ID NO 14
<211> LENGTH: 18
<212> TYPE: PRT
<213> ORGANISM: Gallus gallus

<400> SEQUENCE: 14

Cys Thr Arg Ser Ser Cys Gly Gly Asp Tyr Glu Ala Gly Cys Ile Asp
1               5                   10                  15

Ala Trp

<210> SEQ ID NO 15
<211> LENGTH: 256
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 15

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
                20                  25                  30
```

```
Gly Met Ala Trp Val Arg Gln Ala Pro Gly Lys Gly Leu Glu Phe Val
            35                  40                  45

Ala Gly Ile Ala Tyr Ser Ser Gly Thr Gly Tyr Gly Ser Ala Val
 50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Phe Cys
                85                  90                  95

Ala Lys Ser Ala Asn Ser Gly Asn Pro Asp Ala Gly Glu Ile Asp Ala
            100                 105                 110

Trp Gly His Gly Thr Glu Val Ile Val Ser Ser Gly Gly Gly Ser
            115                 120                 125

Gly Gly Gly Gly Ser Gly Gly Gly Ser Ala Val Leu Ala His Thr
130                 135                 140

Ser Gly Ser Leu Val Gln Ala Ala Leu Thr Glu Pro Ala Ser Val Ser
145                 150                 155                 160

Ala Asn Leu Gly Gly Thr Val Lys Ile Thr Cys Ser Gly Gly Gly Ser
                165                 170                 175

Ser Ser Tyr Tyr Gly Trp Tyr Gln Gln Lys Ser Pro Gly Ser Ala Pro
            180                 185                 190

Val Thr Val Ile Tyr Gln Asp Thr Glu Arg Pro Ser Asn Ile Pro Ser
            195                 200                 205

Arg Phe Ser Gly Ser Thr Ser Gly Ser Thr Ala Thr Leu Thr Ile Thr
            210                 215                 220

Gly Val Gln Ala Asp Asp Glu Ala Val Tyr Phe Cys Gly Asn Glu Asp
225                 230                 235                 240

Ile Thr Tyr Val Gly Val Phe Gly Ala Gly Thr Thr Leu Thr Val Leu
                245                 250                 255

<210> SEQ ID NO 16
<211> LENGTH: 248
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 16

Ala Val Thr Leu Asp Glu Ser Gly Gly Gly Leu Gln Thr Pro Gly Gly
 1               5                  10                  15

Gly Leu Ser Leu Val Cys Lys Ala Ser Gly Phe Thr Phe Ser Ser Tyr
                20                  25                  30

Asp Met Gly Trp Met Arg Gln Ala Pro Gly Lys Gly Leu Glu Phe Ile
            35                  40                  45

Ala Gly Ile Ser Tyr Ser Gly Ser Asp Thr Arg Tyr Gly Ser Ala Val
 50                  55                  60

Gln Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                85                  90                  95

Ala Arg Gly Gly Ala Gly His Asp Ile Asp Arg Trp Gly His Gly Thr
            100                 105                 110

Glu Val Ile Val Ser Ser Gly Gly Gly Ser Gly Gly Gly Gly Ser
            115                 120                 125

Gly Gly Gly Gly Ser Ala Val Leu Ala His Thr Ser Gly Ser Leu Val
```

```
                130                 135                 140
Gln Ala Ala Leu Thr Glu Pro Ala Ser Val Ser Ala Asn Leu Gly Gly
145                 150                 155                 160

Thr Val Lys Ile Thr Cys Ser Gly Ser Ser Gly Ser Tyr Gly Trp Tyr
                165                 170                 175

Gln Gln Lys Ser Pro Gly Ser Ala Pro Val Thr Val Ile Tyr Arg Asn
                180                 185                 190

Asp Lys Arg Pro Ser Asp Ile Pro Ser Arg Phe Ser Gly Ser Lys Ser
                195                 200                 205

Gly Ser Thr Ala Thr Leu Thr Ile Thr Gly Val Gln Ala Glu Asp Glu
                210                 215                 220

Ala Val Tyr Tyr Cys Gly Ser Ala Asp Ser Ser Gly Ala Ile Phe Gly
225                 230                 235                 240

Ala Gly Thr Thr Leu Thr Val Leu
                245
```

<210> SEQ ID NO 17
<211> LENGTH: 255
<212> TYPE: PRT
<213> ORGANISM: Artificial Sequence
<220> FEATURE:
<223> OTHER INFORMATION: VH and VL sequence (from Gallus gallus) with linker peptide

<400> SEQUENCE: 17

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
                20                  25                  30

Gly Met Ala Trp Val Arg Gln Ala Pro Gly Lys Gly Leu Glu Phe Val
                35                  40                  45

Ala Gly Ile Ala Tyr Ser Gly Ser Gly Thr Gly Tyr Gly Ser Ala Val
                50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Ile Tyr Phe Cys
                85                  90                  95

Ala Lys Gly Pro Ser Gly Tyr Arg Tyr Leu Val Gly Asn Asn Ile Asp
                100                 105                 110

Ala Trp Gly His Gly Thr Glu Val Ile Val Ser Ser Gly Gly Gly Gly
                115                 120                 125

Ser Gly Gly Gly Gly Ser Gly Gly Gly Gly Ser Ala Val Leu Ala His
                130                 135                 140

Thr Ser Gly Ser Leu Val Gln Ala Ala Leu Thr Glu Pro Ala Ser Val
145                 150                 155                 160

Ser Ala Asn Leu Gly Gly Thr Val Lys Ile Thr Cys Ser Gly Asp Pro
                165                 170                 175

Thr Tyr Tyr Gly Trp Tyr Gln Lys Lys Ser Pro Gly Ser Ala Pro Val
                180                 185                 190

Thr Leu Ile Tyr Ser Asn Asp Lys Arg Pro Ser Asp Ile Pro Ser Arg
                195                 200                 205

Phe Ser Gly Ser Leu Ser Gly Ser Thr Asn Thr Leu Thr Ile Thr Gly
                210                 215                 220

Val Gln Val Glu Asp Glu Ala Val Tyr Tyr Cys Gly Ser Tyr Asp Ser
225                 230                 235                 240
```

Thr Tyr Asp Ile Ile Phe Gly Ala Gly Thr Thr Leu Thr Val Leu
            245                 250                 255

<210> SEQ ID NO 18
<211> LENGTH: 259
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 18

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Asp Tyr
            20                  25                  30

Gly Met Gln Trp Val Arg Gln Ala Pro Gly Arg Ala Gly Ile Val Ala
            35                  40                  45

Ser Ile Ser Asn Ser Gly Ser Arg Thr Tyr Tyr Gly Ala Ala Val Lys
        50                  55                  60

Gly Arg Ala Thr Ile Ser Arg Asp Asp Gly Gln Ser Thr Val Arg Leu
65                  70                  75                  80

Gln Leu Tyr Asp Leu Arg Ala Glu Asp Thr Gly Thr Tyr Tyr Cys Ala
                85                  90                  95

Arg Thr Ala Gly Gly Cys Tyr Ala Cys Ala Asp Asp Ile Asp Ala Trp
            100                 105                 110

Gly His Gly Thr Glu Val Ile Val Ser Ser Gly Gly Gly Gly Ser Gly
            115                 120                 125

Gly Gly Gly Ser Gly Gly Gly Ser Ala Val Leu Ala His Thr Ser
        130                 135                 140

Gly Ser Leu Val Gln Ala Ala Leu Thr Glu Pro Ala Ser Val Ser Ala
145                 150                 155                 160

Asn Leu Gly Gly Thr Val Lys Ile Thr Cys Ser Val Asp Ile Ile Asp
                165                 170                 175

Asp Val Thr Tyr Tyr Tyr Gly Trp His Gln Gln Lys Ser Pro Gly Ser
            180                 185                 190

Ala Pro Val Thr Val Ile Tyr Gly Asp Asn Gln Arg Pro Ser Asp Ile
            195                 200                 205

Pro Ser Arg Phe Ser Gly Ser Ala Ser Gly Ser Thr Ala Thr Leu Thr
        210                 215                 220

Ile Thr Gly Val Gln Ala Asp Asp Glu Ala Val Tyr Phe Cys Gly Ala
225                 230                 235                 240

Tyr Asp Ser Ser Asp Asp Val Ala Ile Phe Gly Ala Gly Thr Thr Leu
                245                 250                 255

Thr Val Leu

<210> SEQ ID NO 19
<211> LENGTH: 258
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 19

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser His

```
              20                  25                  30
Gly Met Gly Trp Val Arg Gln Ala Pro Gly Lys Gly Leu Glu Phe Val
         35                  40                  45
Ala Ser Ile Ser Asn Thr Gly Gly Thr Ala Tyr Gly Ala Ala Val
 50                  55                  60
Lys Gly Arg Ala Thr Ile Ser Arg Asp Asn Gly Gln Ser Thr Val Arg
 65                  70                  75                  80
Leu Gln Leu Asn Asn Leu Arg Ala Asp Asp Thr Ala Thr Tyr Tyr Cys
                 85                  90                  95
Ala Arg Ala Pro Ser Ser Gly Tyr Cys Asn Asn Val His Ile Val Asp
             100                 105                 110
Ile Ile Asp Thr Trp Gly His Gly Thr Glu Val Ile Val Ser Ser Gly
         115                 120                 125
Gly Gly Gly Ser Gly Gly Gly Ser Gly Gly Gly Ser Ala Val
     130                 135                 140
Leu Ala His Thr Ser Gly Ser Leu Val Gln Ala Ala Leu Thr Glu Pro
145                 150                 155                 160
Ala Ser Val Ser Ala Asn Leu Gly Gly Thr Val Lys Ile Thr Cys Ser
                 165                 170                 175
Gly Gly Ser Gly Tyr Tyr Gly Trp Phe Gln Gln Lys Ser Pro Gly Ser
             180                 185                 190
Ala Pro Val Thr Val Ile Tyr Glu Asn Thr Lys Arg Pro Ser Asp Ile
         195                 200                 205
Pro Ser Arg Phe Ser Gly Ser Ala Ser Gly Ser Thr Ala Thr Leu Thr
     210                 215                 220
Ile Thr Gly Val Gln Val Glu Asp Glu Ala Val Tyr Tyr Cys Gly Asn
225                 230                 235                 240
Arg Asp Ile Ser Tyr Val Ala Ile Phe Gly Ala Gly Thr Thr Leu Thr
                 245                 250                 255
Val Leu

<210> SEQ ID NO 20
<211> LENGTH: 256
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 20

Ala Val Thr Leu Asp Glu Ser Gly Gly Gly Leu Gln Thr Pro Gly Gly
 1               5                  10                  15
Gly Leu Ser Leu Val Cys Lys Ala Ser Gly Phe Thr Phe Ser Asp Tyr
                 20                  25                  30
Gly Met Gly Trp Met Arg Gln Ala Pro Gly Lys Gly Leu Glu Trp Val
         35                  40                  45
Ala Ser Val Thr Tyr Thr Gly Asp Glu Thr Pro Phe Tyr Ala Pro Ala
     50                  55                  60
Val Gln Gly Arg Ala Thr Ile Ser Arg Asp Asn Gly Gln Ser Thr Val
 65                  70                  75                  80
Arg Leu Gln Leu Asn Ser Leu Arg Ala Glu Asp Thr Ala Thr Tyr Phe
                 85                  90                  95
Cys Ala Lys Ser Pro Asn Ser Gly Ile Pro Asn Gly Ala Phe Ile Asp
             100                 105                 110
Thr Trp Gly His Gly Thr Glu Val Ile Val Ser Ser Gly Gly Gly Gly
```

```
                    115                 120                 125
Ser Gly Gly Gly Gly Ser Gly Gly Gly Ser Ala Val Leu Ala His
    130                 135                 140

Thr Ser Gly Ser Leu Val Gln Ala Ala Leu Thr Glu Pro Ala Ser Val
145                 150                 155                 160

Ser Ala Asn Leu Gly Gly Thr Val Lys Ile Thr Cys Ser Gly Ser Ser
                165                 170                 175

Gly Ser Tyr Gly Trp Tyr Gln Gln Lys Ser Pro Gly Ser Ala Pro Val
            180                 185                 190

Thr Val Ile Tyr Ala Asp Thr Lys Arg Pro Ser Asp Ile Pro Ser Arg
        195                 200                 205

Phe Ser Gly Ser Lys Ser Gly Ser Thr Gly Thr Leu Thr Ile Thr Gly
    210                 215                 220

Val Gln Ala Glu Asp Glu Ala Val Tyr Phe Cys Gly Gly Tyr Glu Asp
225                 230                 235                 240

Gly Thr Asp Val Gly Ile Phe Gly Ala Gly Thr Thr Leu Thr Val Leu
                245                 250                 255

<210> SEQ ID NO 21
<211> LENGTH: 256
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 21

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Asp Tyr
            20                  25                  30

Gly Met Gly Trp Met Arg Gln Ala Pro Gly Lys Gly Leu Glu Trp Val
        35                  40                  45

Ala Ser Val Thr Tyr Thr Gly Asp Glu Thr Pro Phe Tyr Ala Pro Ala
    50                  55                  60

Val Gln Gly Arg Ala Thr Ile Ser Arg Asp Asn Gly Gln Ser Thr Val
65                  70                  75                  80

Arg Leu Gln Leu Asn Ser Leu Arg Ala Glu Asp Thr Ala Thr Tyr Phe
                85                  90                  95

Cys Ala Lys Ser Pro Asn Ser Gly Ile Pro Asn Gly Ala Phe Ile Asp
            100                 105                 110

Thr Trp Gly His Gly Thr Glu Val Ile Val Ser Ser Gly Gly Gly Gly
        115                 120                 125

Ser Gly Gly Gly Gly Ser Gly Gly Gly Ser Ala Val Leu Ala His
    130                 135                 140

Thr Ser Gly Ser Leu Val Gln Ala Ala Leu Thr Glu Pro Ala Ser Val
145                 150                 155                 160

Ser Ala Asn Leu Gly Gly Thr Val Lys Ile Thr Cys Ser Gly Ser Ser
                165                 170                 175

Gly Ser Tyr Gly Trp Tyr Gln Gln Lys Ser Pro Gly Ser Ala Pro Val
            180                 185                 190

Thr Val Ile Tyr Ala Asp Thr Lys Arg Pro Ser Asp Ile Pro Ser Arg
        195                 200                 205

Phe Ser Gly Ser Thr Ser Gly Ser Thr Gly Thr Leu Thr Ile Thr Gly
    210                 215                 220
```

Val Gln Ala Glu Asp Glu Ala Val Tyr Phe Cys Gly Gly Tyr Glu Asp
225                 230                 235                 240

Gly Thr Asp Val Gly Ile Phe Gly Ala Gly Thr Thr Leu Thr Val Leu
            245                 250                 255

<210> SEQ ID NO 22
<211> LENGTH: 256
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 22

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Asp Tyr
            20                  25                  30

Gly Met Gly Trp Met Arg Gln Ala Pro Gly Lys Gly Leu Glu Trp Val
        35                  40                  45

Ala Ser Val Thr Tyr Thr Gly Asp Glu Thr Pro Phe Tyr Ala Pro Ala
    50                  55                  60

Val Gln Gly Arg Ala Thr Ile Ser Arg Asp Asn Gly Gln Ser Thr Val
65                  70                  75                  80

Arg Leu Gln Leu Asn Ser Leu Arg Ala Glu Asp Thr Ala Thr Tyr Phe
                85                  90                  95

Cys Ala Lys Ser Pro Asn Ser Gly Ile Pro Asn Gly Ala Phe Ile Asp
            100                 105                 110

Thr Trp Gly His Gly Thr Glu Val Ile Val Ser Ser Gly Gly Gly Gly
        115                 120                 125

Ser Gly Gly Gly Gly Ser Gly Gly Gly Ser Ala Val Leu Ala His
    130                 135                 140

Thr Ser Gly Ser Leu Val Gln Ala Ala Leu Thr Glu Pro Ala Ser Val
145                 150                 155                 160

Ser Ala Asn Leu Gly Gly Thr Val Lys Ile Thr Cys Ser Gly Ser Ser
                165                 170                 175

Gly Ser Tyr Gly Trp Tyr Gln Gln Lys Ser Pro Gly Ser Ala Pro Val
            180                 185                 190

Thr Val Ile Tyr Ala Asp Thr Lys Arg Pro Ser Asp Ile Pro Ser Arg
        195                 200                 205

Phe Ser Gly Ser Thr Ser Asp Ser Thr Gly Thr Leu Thr Ile Thr Gly
    210                 215                 220

Val Gln Ala Glu Asp Glu Ala Val Tyr Phe Cys Gly Gly Tyr Glu Asp
225                 230                 235                 240

Gly Thr Asp Val Gly Ile Phe Gly Ala Gly Thr Thr Leu Thr Val Leu
                245                 250                 255

<210> SEQ ID NO 23
<211> LENGTH: 256
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 23

Ala Val Thr Leu Asp Glu Ser Gly Gly Gly Leu Gln Thr Pro Gly Gly
1               5                   10                  15

```
Gly Leu Ser Leu Val Cys Lys Ala Ser Gly Phe Thr Phe Ser Asp Tyr
                20                  25                  30

Gly Met Gly Trp Met Arg Gln Ala Pro Gly Lys Gly Leu Glu Trp Val
            35                  40                  45

Ala Ser Val Thr Tyr Thr Gly Asp Glu Thr Pro Phe Tyr Ala Pro Ala
        50                  55                  60

Val Gln Gly Arg Ala Thr Ile Ser Arg Asp Asn Gly Gln Ser Thr Val
 65                  70                  75                  80

Arg Leu Gln Leu Asn Ser Leu Arg Ala Glu Asp Thr Ala Thr Tyr Phe
                85                  90                  95

Cys Ala Lys Ser Pro Asn Ser Gly Ile Pro Asn Gly Ala Phe Ile Asp
               100                 105                 110

Thr Trp Gly His Gly Thr Glu Val Ile Val Ser Ser Gly Gly Gly Gly
           115                 120                 125

Ser Gly Gly Gly Gly Ser Gly Gly Gly Ser Ala Val Leu Ala His
       130                 135                 140

Thr Ser Gly Ser Leu Val Gln Ala Ala Leu Thr Glu Pro Ala Ser Val
145                 150                 155                 160

Ser Ala Asn Leu Gly Gly Thr Val Lys Ile Thr Cys Ser Gly Ser Ser
               165                 170                 175

Gly Ser Tyr Gly Trp Tyr Gln Gln Lys Ser Pro Gly Ser Ala Pro Val
           180                 185                 190

Thr Val Ile Tyr Ala Asn Thr Asn Arg Pro Ser Asp Ile Pro Ser Arg
       195                 200                 205

Phe Ser Gly Ser Lys Ser Gly Ser Thr Ala Thr Leu Thr Ile Thr Gly
210                 215                 220

Val Gln Ala Glu Asp Glu Ala Val Tyr Phe Cys Gly Gly Tyr Glu Asp
225                 230                 235                 240

Gly Thr Asp Val Gly Ile Phe Gly Ala Gly Thr Thr Leu Thr Val Leu
               245                 250                 255

<210> SEQ ID NO 24
<211> LENGTH: 256
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 24

Ala Val Thr Leu Asp Glu Ser Gly Gly Leu Gln Thr Pro Gly Gly
 1               5                  10                  15

Gly Leu Ser Leu Val Cys Lys Ala Ser Gly Phe Thr Phe Ser Asp Tyr
                20                  25                  30

Gly Met Gly Trp Met Arg Gln Ala Pro Gly Lys Gly Leu Glu Trp Val
            35                  40                  45

Ala Ser Val Thr Tyr Thr Gly Asp Glu Thr Pro Phe Tyr Ala Pro Ala
        50                  55                  60

Val Gln Gly Arg Ala Thr Ile Ser Arg Asp Asn Gly Gln Ser Thr Val
 65                  70                  75                  80

Arg Leu Gln Leu Asn Ser Leu Arg Ala Glu Asp Thr Ala Thr Tyr Phe
                85                  90                  95

Cys Ala Lys Ser Pro Asn Ser Gly Ile Pro Asn Gly Ala Phe Ile Asp
               100                 105                 110

Thr Trp Gly His Gly Thr Glu Val Ile Val Ser Ser Gly Gly Gly Gly
           115                 120                 125
```

```
Ser Gly Gly Gly Gly Ser Gly Gly Gly Ser Ala Val Leu Ala His
        130                 135                 140

Thr Ser Gly Ser Leu Val Gln Ala Ala Leu Thr Glu Pro Ala Ser Val
145                 150                 155                 160

Ser Ala Asn Leu Gly Gly Thr Val Lys Ile Thr Cys Ser Gly Ser Ser
                165                 170                 175

Gly Ser Tyr Gly Trp Tyr Gln Gln Lys Ser Pro Gly Ser Ala Pro Val
            180                 185                 190

Thr Val Ile Tyr Ala Asn Thr Asn Arg Pro Ser Asp Ile Pro Ser Arg
        195                 200                 205

Phe Ser Gly Ser Pro Ser Gly Ser Thr Ala Thr Leu Thr Ile Thr Gly
        210                 215                 220

Val Gln Ala Glu Asp Glu Ala Val Tyr Phe Cys Gly Gly Tyr Glu Asp
225                 230                 235                 240

Gly Thr Asp Val Gly Ile Phe Gly Ala Gly Thr Thr Leu Thr Val Leu
                245                 250                 255

<210> SEQ ID NO 25
<211> LENGTH: 259
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 25

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Asp Tyr
                20                  25                  30

Gly Met Gly Trp Met Arg Gln Ala Pro Gly Lys Gly Leu Glu Trp Val
            35                  40                  45

Ala Gly Ile Ser Ser Ser Gly Ser Asp Thr Tyr Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Thr Glu Asp Thr Ala Thr Tyr Phe Cys
                85                  90                  95

Ala Lys Ser Ala Asn Asn Met Cys Asp Asn Thr Gly Cys Ala Ala Gly
                100                 105                 110

Gln Ile Asp Thr Trp Gly His Gly Thr Glu Val Ile Val Ser Ser Gly
            115                 120                 125

Gly Gly Gly Ser Gly Gly Gly Gly Ser Gly Gly Gly Ser Ala Val
        130                 135                 140

Leu Ala His Thr Ser Gly Ser Leu Val Gln Ala Ala Leu Thr Glu Pro
145                 150                 155                 160

Ala Ser Val Ser Ala Asn Leu Gly Gly Thr Val Lys Ile Thr Cys Ser
                165                 170                 175

Gly Gly Ser Gly Arg Tyr Gly Trp Tyr Gln Gln Lys Ser Pro Gly Ser
            180                 185                 190

Ala Pro Val Thr Val Ile Tyr Ala Asp Thr Asn Arg Pro Ser Asp Ile
        195                 200                 205

Pro Ser Arg Phe Ser Gly Ser Lys Ser Gly Ser Thr Ala Thr Leu Thr
        210                 215                 220

Ile Thr Gly Val Gln Ala Asp Asp Glu Ala Val Tyr Tyr Cys Gly Asn
```

```
                      225                 230                 235                 240

Tyr Glu Gly Gly Phe Phe Asn Asp Ile Phe Gly Ala Gly Thr Thr Leu
                  245                 250                 255

Thr Val Leu

<210> SEQ ID NO 26
<211> LENGTH: 259
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 26

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Asp Tyr
                20                  25                  30

Gly Met Gly Trp Met Arg Gln Ala Pro Gly Lys Gly Leu Glu Trp Val
            35                  40                  45

Ala Gly Ile Gly Ser Thr Gly Ser Ser Thr Tyr Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Thr Glu Asp Thr Ala Thr Tyr Phe Cys
                85                  90                  95

Ala Lys Ser Ala Asn Asn Met Cys Asp Asn Thr Gly Cys Ala Ala Gly
            100                 105                 110

Gln Ile Asp Thr Trp Gly His Gly Thr Glu Val Ile Val Ser Ser Gly
        115                 120                 125

Gly Gly Gly Ser Gly Gly Gly Ser Gly Gly Gly Ser Ala Val
130                 135                 140

Leu Ala His Thr Ser Gly Ser Leu Val Gln Ala Ala Leu Thr Glu Pro
145                 150                 155                 160

Ala Ser Val Ser Ala Asn Leu Gly Gly Thr Val Lys Ile Thr Cys Ser
                165                 170                 175

Gly Gly Ser Gly Arg Tyr Gly Trp Tyr Gln Gln Lys Ser Pro Gly Ser
            180                 185                 190

Ala Pro Val Thr Val Ile Tyr Ala Asp Thr Asn Arg Pro Ser Asp Ile
        195                 200                 205

Pro Ser Arg Phe Ser Gly Ser Lys Ser Gly Ser Thr Ala Thr Leu Thr
    210                 215                 220

Ile Thr Gly Val Gln Ala Asp Asp Glu Ala Val Tyr Tyr Cys Gly Asn
225                 230                 235                 240

Tyr Glu Gly Gly Phe Phe Asn Asp Ile Phe Gly Ala Gly Thr Thr Leu
                245                 250                 255

Thr Val Leu

<210> SEQ ID NO 27
<211> LENGTH: 255
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 27
```

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Tyr Val
        35                  40                  45

Ala Ser Ile Thr Ser Ile Asp Asp Gly Glu Thr Pro Phe Tyr Ala Pro
    50                  55                  60

Ala Val Gln Gly Arg Ala Thr Ile Ser Arg Asp Asp Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Thr Lys Ser Pro Asn Ser Gly Ile Pro Asn Gly Ala Phe Ile
            100                 105                 110

Asp Thr Trp Gly His Gly Thr Glu Val Ile Val Ser Ser Gly Gly Gly
            115                 120                 125

Gly Ser Gly Gly Gly Gly Ser Gly Gly Gly Gly Ser Ala Val Leu Ala
            130                 135                 140

His Thr Ser Gly Ser Leu Val Gln Ala Ala Leu Thr Glu Pro Ala Ser
145                 150                 155                 160

Val Ser Ala Asn Leu Gly Gly Thr Val Lys Ile Thr Cys Ser Gly Gly
                165                 170                 175

Gly Asn Asn Tyr Gly Trp His Gln Gln Lys Ser Pro Gly Ser Ala Pro
            180                 185                 190

Val Thr Val Ile Tyr Ser Asn Asp Lys Arg Pro Ser Asp Ile Pro Ser
            195                 200                 205

Arg Phe Ser Gly Ser Ala Ser Gly Ser Thr Gly Thr Leu Thr Ile Thr
210                 215                 220

Gly Val Gln Ala Glu Asp Glu Ala Val Tyr Phe Cys Gly Gly Tyr Asp
225                 230                 235                 240

Gly Asn Asn Gly Ala Phe Gly Ala Gly Thr Thr Leu Thr Val Leu
            245                 250                 255

<210> SEQ ID NO 28
<211> LENGTH: 255
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 28

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Tyr Val
        35                  40                  45

Ala Ser Ile Thr Ser Ile Asp Asp Gly Glu Thr Pro Phe Tyr Ala Pro
    50                  55                  60

Ala Val Gln Gly Arg Ala Thr Ile Ser Arg Asp Asp Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Thr Lys Ser Pro Asn Ser Gly Ile Pro Asn Gly Ala Phe Ile
            100                 105                 110

```
Asp Thr Trp Gly His Gly Thr Glu Val Ile Val Ser Ser Gly Gly Gly
        115                 120                 125

Gly Ser Gly Gly Gly Gly Ser Gly Gly Gly Gly Ser Ala Val Leu Ala
    130                 135                 140

His Thr Ser Gly Ser Leu Val Gln Ala Ala Leu Thr Glu Pro Ala Ser
145                 150                 155                 160

Val Ser Ala Asn Leu Gly Gly Thr Val Lys Ile Thr Cys Ser Gly Gly
                165                 170                 175

Gly Asn Asn Tyr Gly Trp His Gln Gln Lys Ser Pro Gly Ser Ala Pro
            180                 185                 190

Val Thr Val Ile Tyr Ser Ser Asp Lys Arg Pro Ser Asp Ile Pro Ser
        195                 200                 205

Arg Phe Ser Gly Ser Ala Ser Gly Ser Thr Gly Thr Leu Thr Ile Thr
    210                 215                 220

Gly Val Gln Val Glu Asp Glu Ala Val Tyr Phe Cys Gly Gly Tyr Asp
225                 230                 235                 240

Gly Asn Asn Gly Ala Phe Gly Ala Gly Thr Thr Leu Thr Val Leu
                245                 250                 255
```

<210> SEQ ID NO 29
<211> LENGTH: 255
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 29

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Tyr Val
        35                  40                  45

Ala Ser Ile Thr Ser Ile Asp Asp Gly Glu Thr Pro Phe Tyr Ala Pro
    50                  55                  60

Ala Val Gln Gly Arg Ala Thr Ile Ser Arg Asp Asp Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Thr Lys Ser Pro Asn Ser Gly Ile Pro Asn Gly Ala Phe Ile
            100                 105                 110

Asp Thr Trp Gly His Gly Thr Glu Val Ile Val Ser Ser Gly Gly Gly
        115                 120                 125

Gly Ser Gly Gly Gly Gly Ser Gly Gly Gly Gly Ser Ala Val Leu Ala
    130                 135                 140

His Thr Ser Gly Ser Leu Val Gln Ala Ala Leu Thr Glu Pro Ala Ser
145                 150                 155                 160

Val Ser Ala Asn Leu Gly Gly Thr Val Lys Ile Thr Cys Ser Gly Gly
                165                 170                 175

Gly Asn Asn Tyr Gly Trp His Gln Gln Lys Ser Pro Gly Ser Ala Pro
            180                 185                 190

Val Thr Val Ile Tyr Ser Thr Asp Lys Arg Pro Ser Asp Ile Pro Ser
        195                 200                 205

Arg Phe Ser Gly Ser Ala Ser Gly Ser Thr Ala Thr Leu Thr Ile Thr
```

```
Gly Val Gln Val Glu Asp Glu Ala Val Tyr Phe Cys Gly Gly Tyr Asp
225                 230                 235                 240

Gly Asn Asn Gly Ala Phe Gly Ala Gly Thr Thr Leu Thr Val Leu
                245                 250                 255
```

<210> SEQ ID NO 30
<211> LENGTH: 257
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 30

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Asn Asp Tyr
                20                  25                  30

Gly Met Gly Trp Met Arg Gln Ala Pro Gly Lys Gly Leu Glu Phe Val
            35                  40                  45

Ala Ser Ile Thr Ser Ala Thr Asp Asn Glu Thr Pro Phe Tyr Ala Pro
50                  55                  60

Ala Val Gln Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Tyr Cys Ala Lys Ser Pro Asn Ser Gly Ile Pro Asn Gly Ala Phe Thr
            100                 105                 110

Asp Thr Trp Gly His Gly Thr Glu Val Ile Val Ser Ser Gly Gly Gly
            115                 120                 125

Gly Ser Gly Gly Gly Gly Ser Gly Gly Gly Gly Ser Ala Val Leu Ala
130                 135                 140

His Thr Ser Gly Ser Leu Val Gln Ala Ala Leu Thr Glu Pro Ala Ser
145                 150                 155                 160

Val Ser Ala Asn Leu Gly Gly Thr Val Lys Ile Thr Cys Ser Gly Ser
                165                 170                 175

Arg Gly Ser Tyr Gly Trp Tyr Gln Gln Lys Ser Pro Gly Ser Ala Pro
            180                 185                 190

Val Thr Val Ile Tyr Ser Asn Asp Lys Arg Pro Ser Asp Ile Pro Ser
            195                 200                 205

Arg Phe Ser Gly Ser Arg Ser Gly Ser Thr Ala Thr Leu Ile Ile Thr
210                 215                 220

Gly Val Arg Ala Glu Asp Glu Ala Val Tyr Phe Cys Gly Ser Tyr Glu
225                 230                 235                 240

Gly Gly Phe Phe Asn Asp Ile Phe Gly Ala Gly Thr Thr Leu Thr Val
                245                 250                 255

Leu
```

<210> SEQ ID NO 31
<211> LENGTH: 249
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 31

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Asn Phe Ser Asp Tyr
            20                  25                  30

Asn Met Gly Trp Val Arg Gln Ala Pro Gly Lys Gly Leu Glu Trp Val
        35                  40                  45

Ala Gly Ile Tyr Ser Gly Tyr Asp Thr Tyr Ala Thr Ala Val Asp
    50                  55                  60

Gly Arg Ala Thr Ile Ser Arg Asp Asp Gly Gln Thr Thr Val Arg Leu
65                  70                  75                  80

Gln Leu Asp Asp Leu Arg Ala Glu Asp Thr Gly Thr Tyr Phe Cys Thr
                85                  90                  95

Arg Gly Ala Ala Pro Tyr Tyr Ile Asp Thr Trp Gly His Gly Thr Glu
                100                 105                 110

Val Ile Val Ser Ser Gly Gly Gly Ser Gly Gly Gly Gly Ser Gly
            115                 120                 125

Gly Gly Gly Ser Ala Val Leu Ala His Thr Ser Gly Ser Leu Val Gln
    130                 135                 140

Ala Ala Leu Thr Glu Pro Ala Ser Val Ser Ala Asn Leu Gly Gly Thr
145                 150                 155                 160

Val Lys Ile Thr Cys Ser Gly Ser Ser Gly Ser Tyr Gly Trp Tyr Gln
                165                 170                 175

Gln Lys Ser Pro Gly Ser Ala Pro Val Thr Val Ile Tyr Ala Asp Thr
                180                 185                 190

Lys Arg Pro Ser Asp Ile Pro Ser Arg Phe Ser Gly Ser Thr Ser Gly
                195                 200                 205

Ser Thr Ser Thr Leu Thr Ile Thr Gly Val Gln Ala Glu Asp Glu Ala
            210                 215                 220

Val Tyr Phe Cys Gly Gly Tyr Glu Asp Gly Ile Asp Val Gly Ile Phe
225                 230                 235                 240

Gly Ala Gly Thr Thr Leu Thr Val Leu
                245

<210> SEQ ID NO 32
<211> LENGTH: 259
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 32

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Ala Met Gly Trp Met Arg Gln Ala Pro Gly Lys Gly Leu Glu Phe Val
        35                  40                  45

Ala Gly Ile Arg Gly Asp Gly Ser Ser Thr Trp Tyr Ala Thr Ala Val
    50                  55                  60

Gln Gly His Ala Thr Ile Ser Arg Asp Asp Gly Gln Ser Thr Leu Arg
65                  70                  75                  80

Leu Gln Leu Asn Asn Leu Arg Ala Glu Asp Thr Ala Thr Tyr Phe Cys
                85                  90                  95

Ala Lys Asn Gly Tyr Asp Gly Asn Arg Trp Gly Ala Tyr Ser Ala Asp
```

```
            100                 105                 110
Ser Ile Asp Ala Trp Gly His Gly Thr Glu Val Ile Val Ser Ser Gly
        115                 120                 125

Gly Gly Gly Ser Gly Gly Gly Gly Ser Gly Gly Gly Gly Ser Ala Val
    130                 135                 140

Leu Ala His Thr Ser Gly Ser Leu Val Gln Ala Ala Leu Thr Glu Pro
145                 150                 155                 160

Ala Ser Val Ser Ala Asn Leu Gly Gly Thr Val Lys Ile Thr Cys Ser
                165                 170                 175

Gly Ser Ser Gly Ser Tyr Gly Trp Tyr Gln Gln Lys Ser Pro Gly Ser
            180                 185                 190

Ala Pro Val Thr Val Ile Tyr Ala Asp Thr Lys Arg Pro Ser Asp Ile
        195                 200                 205

Pro Ser Arg Phe Ser Gly Ser Thr Ser Gly Ser Thr Thr Leu Thr
    210                 215                 220

Ile Thr Gly Val Gln Ala Glu Asp Glu Ala Val Tyr Phe Cys Gly Gly
225                 230                 235                 240

Tyr Glu Asp Gly Ile Asp Val Gly Ile Phe Gly Ala Gly Thr Thr Leu
                245                 250                 255

Thr Val Leu

<210> SEQ ID NO 33
<211> LENGTH: 256
<212> TYPE: PRT
<213> ORGANISM: Artificial Sequence
<220> FEATURE:
<223> OTHER INFORMATION: VH and VL sequence (from Gallus gallus) with
      linker peptide

<400> SEQUENCE: 33

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Asp Tyr
            20                  25                  30

Gly Met Gly Trp Met Arg Gln Ala Pro Gly Lys Gly Leu Glu Phe Val
        35                  40                  45

Ala Ser Ile Thr Ser Ser Ile Asp Asn Glu Thr Pro Phe Tyr Ala Pro
    50                  55                  60

Ala Val Gln Gly Arg Ala Thr Ile Ser Arg Asp Asp Gly Gln Ser Thr
65                  70                  75                  80

Val Arg Leu Gln Leu Asn Asp Leu Arg Ala Glu Asp Thr Gly Thr Tyr
                85                  90                  95

Tyr Cys Ala Lys Ser Pro Asn Ser Gly Ile Pro Asn Gly Ala Phe Thr
            100                 105                 110

Glu Thr Trp Gly His Gly Thr Glu Val Ile Val Ser Ser Gly Gly Gly
        115                 120                 125

Gly Ser Gly Gly Gly Gly Ser Gly Gly Gly Gly Ser Ala Val Leu Ala
    130                 135                 140

His Thr Ser Gly Ser Leu Val Gln Ala Ala Leu Thr Glu Pro Ala Ser
145                 150                 155                 160

Val Ser Ala Asn Leu Gly Gly Thr Val Lys Ile Thr Cys Ser Gly Gly
                165                 170                 175

Gly Gly Ser Tyr Tyr Gly Trp Tyr Gln Gln Lys Ser Pro Gly Ser Ala
            180                 185                 190

Pro Val Thr Val Ile Tyr Ser Asn Asn Lys Arg Pro Ser Asp Ile Pro
```

```
                195                 200                 205
Ser Arg Phe Ser Gly Ala Leu Ser Gly Ser Thr Val Thr Leu Thr Ile
    210                 215                 220

Thr Gly Val Gln Ala Glu Asp Glu Ala Val Tyr Tyr Cys Gly Ser Tyr
225                 230                 235                 240

Asp Ser Ser Gly Gly Ile Phe Gly Ala Gly Thr Thr Leu Thr Val Leu
                245                 250                 255
```

<210> SEQ ID NO 34
<211> LENGTH: 254
<212> TYPE: PRT
<213> ORGANISM: Artificial Sequence
<220> FEATURE:
<223> OTHER INFORMATION: VH and VL sequence (from Gallus gallus) with linker peptide

<400> SEQUENCE: 34

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Phe
                20                  25                  30

Asn Met Met Trp Val Arg Gln Ala Pro Gly Lys Ser Leu Glu Trp Val
            35                  40                  45

Ala Gly Ile Gln Asn Ile Gly Ser Gly Thr Asp Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Arg Gly Ala Gly Gly Cys Ala Ser Cys Ala Asp Asp Ile Asp Ala
            100                 105                 110

Trp Gly His Gly Thr Glu Val Ile Val Ser Ser Gly Gly Gly Gly Ser
        115                 120                 125

Gly Gly Gly Gly Ser Gly Gly Gly Ser Ala Val Leu Ala His Thr
    130                 135                 140

Ser Gly Ser Leu Val Gln Ala Ala Leu Thr Glu Pro Ala Ser Val Ser
145                 150                 155                 160

Ala Asn Leu Gly Gly Thr Val Lys Ile Thr Cys Ser Gly Gly Gly Gly
                165                 170                 175

Ser Tyr Tyr Gly Trp Tyr Gln Gln Lys Ser Pro Gly Ser Ala Pro Val
            180                 185                 190

Thr Val Ile Tyr Ser Asn Asn Lys Arg Pro Ser Asp Ile Pro Ser Arg
        195                 200                 205

Phe Ser Gly Ala Leu Ser Gly Ser Thr Val Thr Leu Thr Ile Thr Gly
    210                 215                 220

Val Gln Ala Glu Asp Glu Ala Val Tyr Tyr Cys Gly Ser Tyr Asp Ser
225                 230                 235                 240

Ser Gly Gly Ile Phe Gly Ala Gly Thr Thr Leu Thr Val Leu
                245                 250
```

<210> SEQ ID NO 35
<211> LENGTH: 253
<212> TYPE: PRT
<213> ORGANISM: Artificial Sequence
<220> FEATURE:
<223> OTHER INFORMATION: VH and VL sequence (from Gallus gallus) with linker peptide

```
<400> SEQUENCE: 35

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Ser Tyr
                20                  25                  30

Thr Met Asn Trp Val Arg Gln Ala Pro Gly Lys Gly Leu Glu Trp Val
            35                  40                  45

Ala Gly Ile Asn Asn Phe Gly Asn Thr Thr Leu Arg Val Ala Val Lys
    50                  55                  60

Gly Arg Ala Thr Ile Ser Arg Asp Asn Gly Gln Thr Thr Val Arg Leu
65                  70                  75                  80

Gln Leu Asn Asn Leu Arg Ala Glu Asp Thr Ala Thr Tyr Phe Cys Ala
                85                  90                  95

Lys Asn Ala Ala Gly Ser Cys Ile Asn Cys Ala Asp Asn Ile Asp Val
                100                 105                 110

Trp Gly His Gly Thr Glu Val Ile Val Ser Ser Gly Gly Gly Gly Ser
            115                 120                 125

Gly Gly Gly Gly Ser Gly Gly Gly Ser Ala Val Leu Ala His Thr
    130                 135                 140

Ser Gly Ser Leu Val Gln Ala Ala Leu Thr Glu Pro Ala Ser Val Ser
145                 150                 155                 160

Ala Asn Leu Gly Gly Thr Val Lys Ile Thr Cys Ser Gly Ser Thr Tyr
                165                 170                 175

Asn Tyr Gly Trp Tyr Gln Gln Lys Ser Pro Gly Ser Ala Pro Val Thr
            180                 185                 190

Val Ile Tyr Tyr Asn Asp Lys Arg Pro Ser Gly Ile Pro Ser Arg Phe
    195                 200                 205

Ser Gly Ser Lys Ser Gly Ser Thr Gly Thr Leu Thr Ile Thr Gly Val
        210                 215                 220

Arg Ala Glu Asp Glu Ala Ile Tyr Tyr Cys Ala Gly Tyr Asp Ser Asn
225                 230                 235                 240

Ala Gly Ile Phe Gly Ala Gly Thr Thr Leu Thr Val Leu
                245                 250
```

SEQUENCING CHICKEN ANTIBODY REPERTOIRES FOLLOWING HYPERIMMUNIZATION AND THE IDENTIFICATION OF ANTIGEN-SPECIFIC MONOCLONAL ANTIBODIES

CROSS-REFERENCE TO RELATED APPLICATION

This application is a Section 371 National Stage Application of International Application No. PCT/US 2016/065331, filed Dec. 7, 2016, and published as WO2017/100289 on Jun. 15, 2017, which claims priority to and benefits of U.S. Provisional Patent Application Ser. No. 62/264,090, filed with the United States Patent and Trademark Office on Dec. 7, 2015, the entire contents of which are incorporated herein by reference.

FIELD

This description relates to immunology and more particularly to identifying antibodies following hyperimmunization.

BACKGROUND

Antibodies are the end-product of effector cells of the humoral adaptive immune system. Antibodies are glycoproteins secreted by plasma cells in large numbers; estimates range from several hundred to tens of thousands per second in humans. The functions of antibodies include: opsonization, antibody-dependent cell-mediated cytotoxicity (ADCC), complement fixation, and, neutralization. By definition, antibody-mediated neutralization occurs when binding of the target epitope interferes or negates the function of that targeted biomolecule, usually a receptor or a ligand. Such is the case of a bacterial epitope, where neutralization can manifest as blocking adherence to a mammalian cell, thereby preventing attachment and colonization. In viral neutralization, antibody binding can prevent replication by inhibiting cell entry.

Structurally, an antibody is a heterodimer consisting of two light and two heavy chains covalently attached by disulfide bonds at cysteine residues. Within the two chains, there are regions of conservation and variability, known as $C_L$ and $C_H$, and $V_L$ and $V_H$. The variable heavy and light chain ($V_L$ and $V_H$) interact with antigen while the fourth constant region of the heavy chain ($C_H4$), in the case of chicken IgG, interacts with other immune system proteins or immune cell receptors. Because of their antigen contact, the two variable regions impart specificity for the antibody. Within the two variable regions, there are three key sub-regions known as complementary-determining region (CDR)1, CDR2, and CDR3 that constitute the majority of antibody-antigen interactions. The antibody repertoire is the population of antibodies in an organism at one immunological moment. Depending on what antigen is being presented; new or reoccurring, or whether it invokes a primary or secondary immune response, naïve B cells or memory B cells are terminally differentiated to plasma cells—the only cell able to secrete antibody.

The mammalian primary antibody repertoire is comprised by a diversification mechanism of rearrangement of three gene segments called Variable (V), Diversity (D), and Joining (J)—known as V(D)J recombination. This event occurs prior to antigen interaction and is the primary source of diversity for B cell receptors (BCR), which are the membrane-bound forms of secreted immunoglobulins. V(D)J recombination of the heavy chain instills the variability to the CDRs, and the site where all three gene segments come together is the hypervariable CDR3. As compared to CDRH3 (CDR3 of heavy chain), CDRL3 (CDR3 of light chain) is less diverse because there is no D segment for the light chain gene.

While chickens also undergo V(D)J recombination, the process yields almost no diversity because chickens have only one functional V and J segment per chain. For comparison, mice have 101, 91, and up to 8 functional V gene segments for heavy, kappa, and lambda chains respectively.

Bovine herpesvirus type I (BHV-1) and the opportunistic commensal bacterium *Mannheimia haemolytica* are part of a disease complex collectively known as bovine respiratory disease (BRD), which is a leading cause of morbidity and mortality in North American cattle feedlots. While BRD mortality rates are low, 1.6% in 2011, a major feedlot operation in Texas implicated BRD in 65 to 70% of total death loss from 2001 to 2011. Through high morbidity rates (16.2% in 2011) incurring added treatment costs, BRD can become the costliest disease in chronically infected operations. Administration of antibiotic dosing regardless of symptoms, known as metaphylaxis, is a proven method for reducing the burden of BRD. Evidence for this could be seen in an NAHMS-APHIS survey in 2011 estimating that 21.3% of all calves entering smaller feedlots (1,000-7,999) received metaphylactic treatment. Survey responses from larger operations (8,000 or more) claimed even higher rates of metaphylaxis—53.8%.

Historically, the cattle industry has selected for high-performance animals that sequestered metabolic energy, at the expense of the immune system. Continuous improvement in feedlot management practices has also been effective at significantly reducing rates of respiratory disease. Practices such as minimizing animal stress, through defined separation of calves arriving to the feedlot from different geographical regions, are fundamental to minimizing morbidity and mortality rates from BRD. Another crucial feedlot management practice is vaccine administrations for BRD (96% of all calves on arrival).

SUMMARY

In a first aspect, the present description is directed to a composition comprising a recombinant polypeptide having a binding domain, wherein the binding domain comprises a variable light chain domain and a variable heavy chain domain. The amino acid sequence of the variable heavy chain domain and the variable light chain domain are determined by analysis of the antibody repertoire from birds hyperimmunized with an antigen of interest, wherein the recombinant polypeptide binds the antigen of interest after expression in an expression system. The glycosylation profile of the recombinant polypeptide is determined by the expression system. The recombinant polypeptide may be a recombinant monoclonal antibody. The recombinant polypeptide may be a single-chain variable fragment (scFv) polypeptide. The recombinant polypeptide may be expressed and isolated from an in vitro protein expression system wherein the protein expression systems are selected from bacterial, mammalian, insect, and plant expression systems. The expression system may be a bacterial expression system and the recombinant polypeptide may not be glycosylated. The birds may be chickens. The antigen of interest may be *Mannheimia haemolytica* outer membrane protein (Omp) and/or *M. haemolytica* leukotoxin. The scFv polypeptides may be selected from SEQ ID NO:15-SEQ ID NO:35.

In another aspect, the present description is directed to a composition comprising a recombinant DNA molecule, wherein the recombinant DNA molecule comprises DNA sequences that encode a recombinant polypeptide having a binding domain, wherein the binding domain comprises a variable light chain domain and a variable heavy chain domain. The amino acid sequence of the variable heavy chain domain and the variable light chain domain may be determined by analysis of the antibody repertoire from birds hyperimmunized with an antigen of interest, wherein the recombinant polypeptide binds the antigen of interest after expression in an expression system. The glycosylation profile of the recombinant polypeptide may be determined by the expression system. The recombinant DNA molecule may be expressed in bacterial expression systems, mammalian expressions systems, insect expression systems, plant expression systems or combinations thereof.

In a further aspect, the present description relates to a method for identifying and expressing the binding domains for an antigen. The method includes isolating nucleic acids from peripheral blood mononuclear cells of birds from samples collected prior to hyperimmunization and after hyperimmunization, reverse transcribing the mRNA in the samples after enriching the samples for mRNA, amplifying the variable regions of the heavy chains and light chains of the immunoglobulin genes using primers, sequencing across the majority of light and heavy chain variable regions of the immunoglobulins, identifying variable heavy chain amino acid sequences and variable light chain amino acid sequences and expressing polypeptides comprising the identified variable heavy chain amino acid sequences and variable light chain amino acid sequences in an in vitro expression system. The antigen may be *Mannheimia haemolytica* outer membrane protein (Omp) and/or *M. haemolytica* leukotoxin. The binding domain may be the variable heavy chain and the variable light chain amino acid sequences. The binding domain may be in a scFv polypeptide. The binding domain may include the variable heavy chain and the variable light chain amino acid sequences, the binding domain in a rmAb. The scFv polypeptides may be selected from SEQ ID NO:15-SEQ ID NO:35.

In yet a further aspect, the present description also includes a method for preventing disease in an animal. The method includes administering a composition comprising a recombinant polypeptide having a binding domain capable of binding one or more disease antigens, wherein the binding domain of the recombinant polypeptide comprises amino acid sequences of variable regions from a light chain and a heavy chain identified from the antibody repertoire of birds hyperimmunized with the one or more disease antigens. The recombinant polypeptides may be expressed in a bacterial expression system. The birds may be chickens. The antigen may be an antigen *Mannheimia haemolytica* outer membrane protein (Omp) and/or *M. haemolytica* leukotoxin. The disease may be bovine respiratory disease. The recombinant polypeptide may be a scFv polypeptide. The recombinant polypeptide may be a rmAb.

Definitions

Various terms are defined herein. The singular forms of the terms "a", "an", and "the" as used herein include plural references unless the context clearly dictates otherwise.

The term "hyperimmunization" as used herein refers to a state of immunity that is greater than normal and results in the presence of a larger than normal number of antibodies to a specific antigen.

The term "binding domain" as used herein refers to amino acid sequences needed to form an antigenic binding site.

The term "scFv" as used herein refers to a single chain variable fragment that includes the variable region of the light chain and the variable region of the heavy chain of immunoglobulins.

The term "scFv polypeptide" as used herein refers to a polypeptide that includes amino acid sequences from the variable region of the light chain of immunoglobulins and amino acid sequences from the variable region of the heavy chain of immunoglobulins. The scFv polypeptide can also include amino acid sequences that are linker sequences.

The term "scFv gene" as used herein refers to a nucleic acid molecule that encodes the scFv polypeptide.

The term "recombinant monoclonal antibody" as used herein refers to a monoclonal antibody that is obtained by expression of a recombinant DNA molecule The term "recombinant DNA molecule" as used herein refers to a DNA molecule that encodes a polypeptide that includes a functional binding domain and can bind the antigen of interest. The polypeptides include scFv polypeptides and recombinant monoclonal antibodies.

The term "recombinant polypeptide" as used herein refers to a polypeptide that includes a functional binding domain that can bind the antigen of interest and include scFv polypeptides, recombinant monoclonal antibodies.

The term "antibody repertoire" as used herein refers to the population of antibodies in an organism at one immunological moment.

The term "amplicon" as used herein refers to a piece of DNA or RNA that is the source and/or product of natural or artificial amplification or replication events. It can be formed using various methods including polymerase chain reactions (PCR), ligase chain reactions (LCR), or natural gene duplication.

The term "linker peptide" as used herein refers to a peptide from about five to about 30 amino acids connecting the variable regions of the heavy and light chains of immunoglobulins. The linker peptide is usually rich in glycine, for flexibility and/or serine or threonine for solubility and can either connect the N-terminus of the variable heavy chain and the C-terminus of the variable light chain, or vice versa.

BRIEF DESCRIPTION OF THE FIGURES

FIG. 4A—$V_L$ non-immune state; FIG. 4B—$V_L$ Post-hyperimmunized; FIG. 4C—$V_H$ non-immune state; FIG. 4D—$V_H$ post-hyperimmunized state.

FIGS. 5A-5D are plots of CDR3 read length distributions of the top 5% of repertoire reads for one chicken.

DESCRIPTION OF THE EMBODIMENTS

Figure 1:
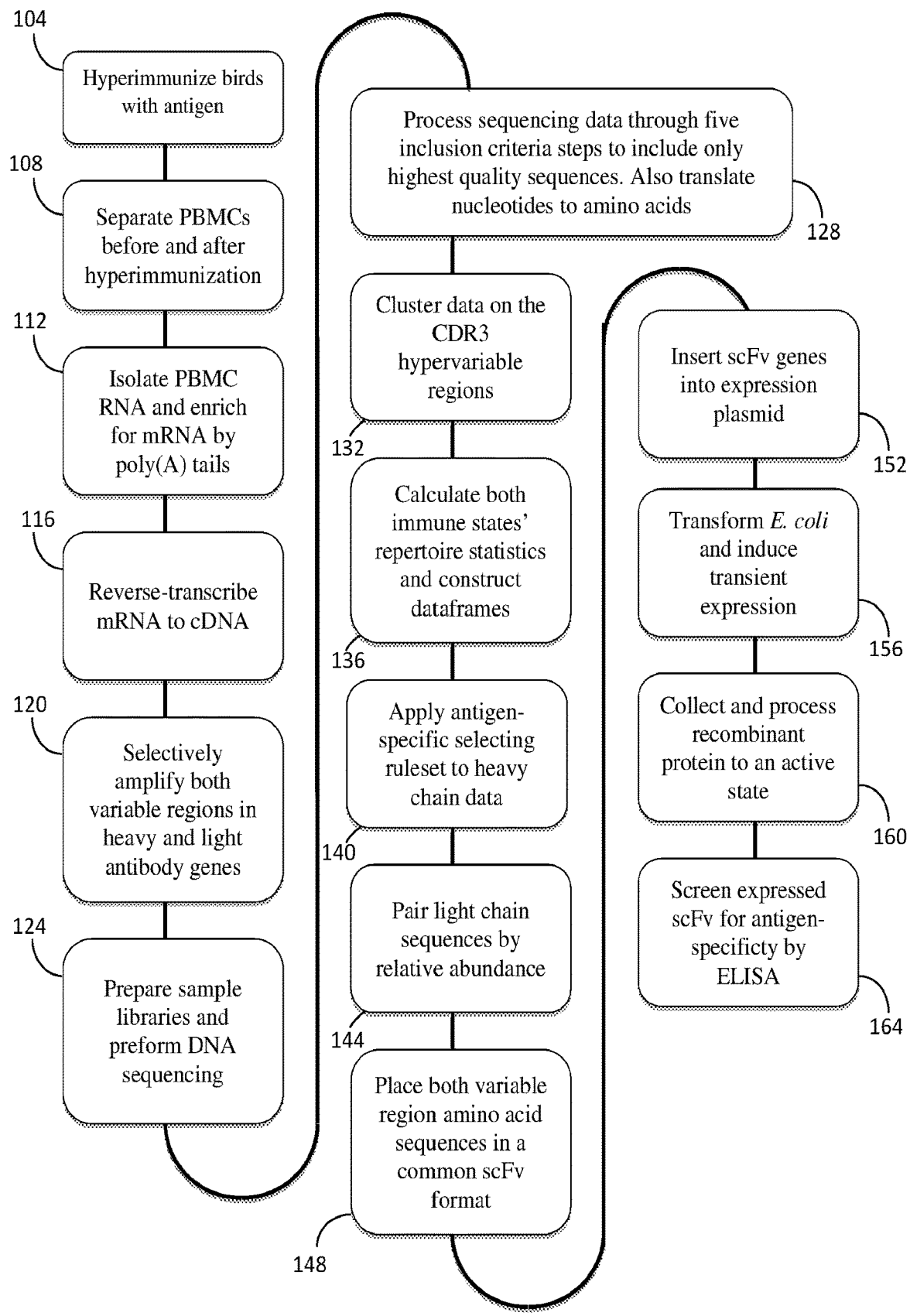
FIG. 1 is a flow chart for a method of identifying and isolating the antigenic binding domains in single chain variable fragments.

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized, and structural, logical, mechanical, electrical, and other changes may be made.

The present description includes methods for identifying the amino acid sequences of binding domains of antibodies in the antibody repertoire generated when birds are hyperimmunized with an antigen of interest. The method also includes expressing the DNA constructs encoding these binding domains in a recombinant expression system. The binding domains, when expressed in the recombinant expression system, can be identified that are able to bind specifically to the antigen of interest. In one embodiment, the binding domains expressed in the recombinant expression system bind and/or neutralize the antigen that was initially used to hyperimmunize the birds. The binding domains can be part of a single-chain variable fragment (scFv) polypeptide and/or they can be part of a recombinant monoclonal antibody (rmAb).

The present description also includes compositions of polypeptides wherein the binding domains of the polypeptides are recombinant products and are capable of binding and/or neutralizing an antigen. In an embodiment, the antigen is the same or similar to the antigen used to hyperimmunize birds. The binding domains of the polypeptides include amino acid sequences from variable regions of a heavy chain immunoglobulin molecule and amino acid sequences from variable regions of a light chain immunoglobulin molecule. The amino acid sequences of the variable regions of the light chain and the heavy chain can be determined based on the antibody repertoire generated due to the hyperimmunization of the bird and the analysis of the resultant mRNA levels in the peripheral mononuclear blood cells (PBMC) of the hyperimmunized bird. The variable regions of the heavy and light chains can be part of a single-chain variable fragment (scFv) polypeptide and/or they can be part of a recombinant monoclonal antibody (rmAb).

The present description can include a method of obtaining antibodies such as monoclonal antibodies. The method can include sequencing across the majority of light and heavy chain variable regions of chicken immunoglobulin genes performed at two immunological time points: a non-immune (naïve) state and a post-hyperimmunization state. Through deep sequencing of immunoglobulin heavy and light chain messenger RNA transcripts, the antibody population dynamics can be examined following an immune response event such as hyperimmunization. Antigen-specific monoclonal antibody sequences can be identified using the methods described herein.

The method may include extended read lengths surpassing 400 base pairs. A study average sequencing depth can exceed $10^6$ unfiltered reads for each antibody chain. Since mRNA can be extracted from unsorted PBMC populations, identification of antigen-specific antibody sequences leveraged the significant disparity of abundance of an individual B cell clone in non-immune and hyperimmunized states. A greedy incremental clustering algorithm, CD-HIT described in Weizhong Li et al. (Bioinformatics, 17 282-283 and Bioinformatics, 18, 77-82), can be used to observe shifts in immune state frequencies and candidate antigen-specific monoclonal antibodies can be defined as products of rare non-immune B cell clones that were massively expanded and can become highly abundant in the post-immunized state. Conditional rule sets can be utilized that require multiple criteria to be met or exceeded. Candidates from a large database can be efficiently selected for, in a nonbiased manner, using this criteria. In one embodiment, 14 candidates were selected from an input pool of over 82,000 sequences.

The candidates can be tested to confirm antigen-specificity via immunoassay screening of transiently expressed recombinant monoclonal antibodies. Identification of suitable rmAb or scFv can then be overexpressed in an in vitro culture system and isolated for therapeutic use. In one embodiment, the scFvs may be expressed in bacterial or mammalian expression systems. In another embodiment, the rmAbs may be expressed in a mammalian expression systems. Other expression systems such as yeast, insects, plants and the like may also be used and all are within the scope of this description.

In one embodiment, the present description can include a method for identifying the amino acid sequences of the binding domains of antibody molecules and expressing these binding domains in a recombinant expression system. FIG. 1 is one embodiment of the method and illustrates a flow chart of the steps than can be performed to identify and express functional binding domains of an antibody that can bind an antigen.

The method can include hyperimmunizing (104) a bird with an antigen of interest. In one embodiment, the bird is a chicken. While the invention is illustrated by the use of chickens to produce avian antibodies, other fowl including turkeys, ducks, geese, ostrich, Emu, pheasant, pigeon, quail, etc. or combination thereof, may be used.

The antigen can be a variety of antigens and can include one or more immunogenic antigen. The immunogen selected for hyperimmunization can be a well-defined antigen with a known antigenic determinant (or epitope) so that the most abundant sequences in the antibody repertoire would be specific for the target of interest. The antigen can be whole microorganisms such as bacteria, viruses, fungi, parasites and the like. The antigen can also be parts of the microorganisms, lysates or macromolecules from the microorganisms. The microorganisms can be, for example, bacteria such as *Pasteurella*, (e.g. *Pasteurella multocida*), *Mannheimia*, (e.g. *Mannheimia haemolytica*) and *Haemophilus* groups, *Mycoplasma*, and viruses of the respiratory groups such as bovine respiratory syncytial virus (BRSV), bovine viral diarrhea (BVD), parainfluenza ($PI_3$), infectious bovine rhinotrocheitus (IBR), swine influenza, ($H_1N_1,H_3N_2$), Rotavirus and combinations of the same. In one embodiment, the antigen is the purified outer membrane protein (OMP) from *Mannheimia haemolytica*. In another embodiment, the antigen is leukotoxin from *M. haemolytica*.

The birds may be administered more than one antigen. In one embodiment, the antigens administered are the purified outer membrane protein (OMP) from *Mannheimia haemolytica* and leukotoxin from *M. haemolytica*.

The birds may be hyperimmunized by a variety of methods and can include administering the antigen by any suitable route that elicits an immune response. The antigen(s) may be administered by, for example, intramuscular, intraperitoneal, sub-cutaneous and/or oral routes. In one embodiment, the antigen(s) is administered intramuscularly in a wing of the bird. A post-hyperimmunization sample may be collected from the bird at about 5 to about 10 days after the last antigen administration. A post-hyperimmunization sample collected outside of this interval is also within the scope of this disclosure. In one embodiment, a post-hyperimmunization sample is collected after about 6 days after the last antigen administration.

Hyperimmunization may include administering multiple doses of one or more antigens and these doses may be administered, for example, at intervals of 1 to 10 days. In one embodiment, the birds were hyperimmunized by administering antigen on day 1, followed by a booster on day 7 and the hyperimmunized sample was collected on day 13. In one embodiment, the amount of antigen in the booster is about the same as the amount in the primary administration. Boosters and primary injections having different amounts of antigens are also within the scope of this description. The use of a booster, the interval between the primary injection and the booster and the interval between the final antigen administration and the sample collection can vary and all are within the scope of the description.

Samples can be collected from the birds prior to hyperimmunization (pre-HI) and after hyperimmunization (post-HI). In one embodiment, the sample collected can be venous blood. After hyperimmuzation, the post-HI samples may also be spleen cells and bone marrow plasma cells. The peripheral blood mononuclear cells can be separated (108) and obtained from the pre-HI sample and from the post-HI sample.

The method can also include analyzing the antibody repertoire of the pre-HI samples and the post-HI samples. Knowing the repertoire prior to hyperimmunization can allow for calculation of clonal frequency changes that can be explained by B cell clonal expansion during the adaptive immune response. Analyzing the antibody repertoire can include, for example, a number of steps that isolate and enrich the desired nucleic acids and identify the prevalent amino acid sequences of the variable regions of antibodies present in the samples. The RNA can be isolated (112) from the pre-HI samples and post-HI samples. The RNA can also be enriched for the mRNA by using a polyA tail enrichment method as described below in the Examples. The mRNA can then be reverse transcribed (116) to cDNA as described below in the Examples.

Figure 2:
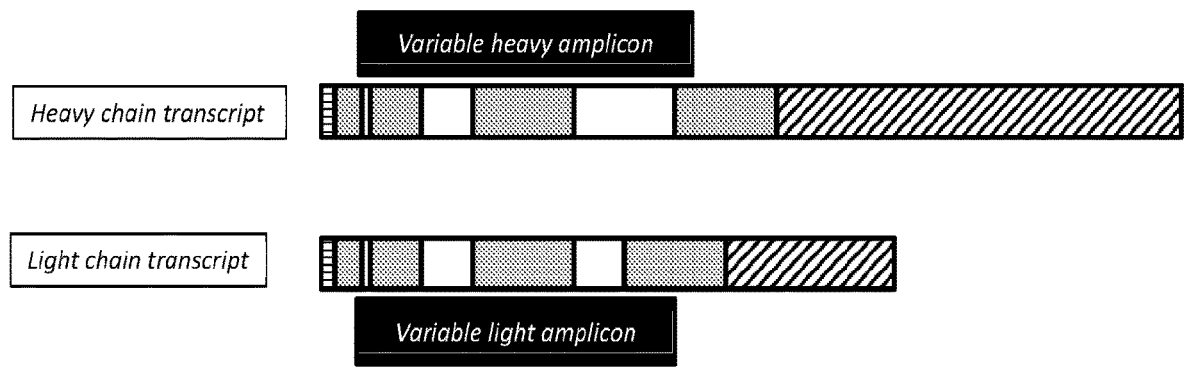
FIG. 2 is a schematic diagram of immunoglobulin gene transcript organization and location of the amplifying primers resulting in amplicons (black). From left to right: Leader sequence (horizontal hash line), Framework 1 region (gray), CDR1 (white), Framework 2 region (gray), CDR2 (white), Framework 3 region (gray), CDR3 (white), Framework 4 region (gray), and Constant regions (diagonal hash line).

The cDNA from the pre-HI samples and the post-HI samples can be selectively amplified (120). The amplification can be targeted to the variable regions of the heavy and light chain antibody genes. Primers can be designed to amplify the variable regions of the light chain genes and the heavy chain genes. FIG. 2 is a schematic diagram of the organization of the transcripts of light chain genes and heavy chain genes in chickens. Primers, for example, can be designed to hybridize in the framework 1 region of the genes and amplify across the three CDRs and into the start of framework 4 as shown in FIG. 2. Primers may be designed to amplify from other locations within and adjacent to the variable regions and all of these are within the scope of this disclosure. In one embodiment, the primers used for amplification include the primer of SEQ ID NO. 1 as the forward variable light ($V_L$) primer, SEQ ID NO. 2 as the reverse $V_L$ primer, SEQ ID NO. 3 as the forward variable heavy ($V_H$) primer, and SEQ ID NO. 4 as the reverse $V_H$ primer. Amplification can be performed by known methods in the art such as using the Polymerase Chain Reaction (PCR).

Amplicons can be generated using the primers and purified. The amplicons can be of variable length depending on the location of the primer and the size of the variable region. Amplicons can be, for example, between about 200 bases and about 1000 bases. In one embodiment, the amplicons can be between about 200 bases and about 500 bases.

The amplicons can be used to generate sample libraries from pre-HI and post-HI samples. The libraries can then be sequenced using high-throughput second generation sequencing. A variety of sequencing methods and strategies can be used. In one embodiment, Ion Torrent sequencing libraries are prepared and sequenced. Other methods of sequencing that can be used include, for example, other second-generation systems such as Illuminia, 454 pyrosequencing, as well as $3^{rd}$ generation systems such as single-molecule real-time sequencing.

The increased throughput of second-generation sequencing, formerly known as next generation sequencing, can be used in antibody repertoire research by expanding the depth of sampling from the repertoire population. Because statistical reasoning can require sequencing depth to exceed the number of samples, second generation sequencing can give a much broader sense of the antibody repertoire. In addition to the increased number of reads, it is also constantly improving its weakness of shorter read lengths. The Ion Torrent platform can increase sequence read lengths from 200 to 400 base pairs. Doubling the read lengths can allow nearly full sequencing of the variable regions; certainly across the three hypervariable regions.

Unfiltered sequence reads can then be passed through inclusion criteria checkpoints (128) selecting for genuine reads. These checkpoints first retain sequences with both the forward and reverse primer sequence. The second inclusion criterion then keeps only those passing the first that also are within the size range of 200 to 500 nucleotides. Nucleotide sequences can be converted to amino acids and only reads in the correct reading frame without stop codons being used.

To assess antibody sequence abundance within the repertoire in the pre-HI and post-HI samples, CDR3 regions of both heavy chains (CDRH3) and light chains (CDRL3) can be isolated by leveraging distinctly conserved flanking residue motifs and clustered by similarity (132). Some highly abundant CDR3s sequences can be identified in the pre- and post-HI samples (136).

In one embodiment, the top four most abundant CDR3 of the heavy chains (CDRH3s) may compose about 4 to about 13% of the repertoire of CDRH3 sequences in the post-HI samples. Additionally, the four most dominant CDRH3s from the post-HI sample antibody repertoires can be found to be minimally contributing to the pre-HI sample antibody repertoire at 0.221-1.499%. The four most dominant CDRH3 sequences in the antibody repertoire of the pre-HI sample may be seen at a similar frequency of about 2-20%, but these sequences can minimally contribute to the antibody repertoire in the post-HI samples at about 0.317 to about 1.8%.

Amino acid sequences of variable heavy chains can be identified as described herein (140). In order to express a functional binding domain, variable light chain sequences may be identified that can be paired with the variable heavy chain amino acid sequences. The pairing of the variable light chain amino acid sequences with the variable heavy chain amino acid sequences may be determined by identifying light chain amino acid sequences that are approximately similar in abundance (144) to the amino acid sequences of variable heavy chains. This can provide compatible $V_H$ amino acid sequences and $V_L$ amino acid sequences that can lead to the expression of a functional binding domain that binds an antigen.

In one embodiment, the $V_H$ amino acid sequences and $V_L$ amino acid sequences may be combined to form a functional domain and the combination may be similar to the combination of $V_H$ amino acid sequences and $V_L$ amino acid sequences seen in vivo in the chickens. In some embodiments, $V_H$ amino acid sequences and $V_L$ amino acid sequences can be combined that are compatible for binding an antigen even though they may not be a naturally occurring combination of $V_H$ amino acid sequences and $V_L$ amino acid sequences in the chicken.

In order to isolate $V_H$ amino acid sequences and $V_L$ amino acid sequences that can lead to the expression of a functional binding domain that binds an antigen, a recombinant DNA molecule can be constructed that includes a gene encoding the $V_H$ amino acid sequences and $V_L$ amino acid sequences, e.g. a scFv gene (148). The recombinant DNA molecule can also include other genes, e.g. ampicillin resistance, and elements, e.g. regulatory elements, necessary for expression of the $V_H$ amino acid sequences and $V_L$ amino acid sequences in an expression system. In one embodiment, the recombinant DNA molecule can include a scFv gene that encodes $V_H$ amino acid sequences and $V_L$ amino acid sequences. In another embodiment the recombinant DNA molecule can include a rmAb gene(s) that encodes a rmAb that include the $V_H$ amino acid sequences and $V_L$ amino acid sequences.

Due to the redundancy in the genetic code, there can be variation in the nucleic acid sequences of an scFv gene that corresponds to a scFv polypeptide. In other words, there can be more than one scFv gene that encodes for a specific polypeptide. For example, the scFv amino acid sequence as shown in SEQ ID NO: 15 can be encoded by variants of a scFv gene. Therefore, all of the scFv genes with nucleic acid sequences, when expressed, resulting in the expression of SEQ ID NO:15 are within the scope of this disclosure. Any scFv genes that encode an identified scFv polypeptide are within the scope of this disclosure.

The nucleic acid sequence of an scFv gene corresponding to an scFv polypeptide can be synthesized to optimize gene expression for the selected gene expression system. The optimization of the nucleic acid sequence of the scFv gene can include, for example, optimizing the nucleic acid sequence of each scFv gene based on codon usage in the desired expression system. In addition, other factors that improve the expression of scFv genes can include codon adaptability, mRNA structure and the like. In one embodiment, the amino acid sequences of the scFv polypeptide can be provided to a commercial gene synthesis vendor, e.g. GenScript in Piscataway, N.J. The nucleic acid sequence of the scFv gene can be determined by algorithms that identify the optimal codons based on the desired expression system, e.g. E. coli expression system and on the specific amino acid sequence desired.

Expression of $V_H$ amino acid sequences and $V_L$ amino acid sequences can be achieved using a variety of techniques. The $V_H$ amino acid sequences and $V_L$ amino acid sequences can be expressed as a recombinant polypeptide with a functional binding domain. The recombinant polypeptide can be a scFv polypeptide, a rmAb and the like.

The scFv gene encoding the encoding a $V_H$ amino acid sequence and a $V_L$ amino acid sequence may by inserted into an expression system (152). The expression system can include an expression plasmid. The scFv gene can be inserted into an expression plasmid where the scFv gene will be expressed to form the corresponding scFv polypeptide. A variety of suitable expression systems and expression plasmids are known and can be suitable in the expression of scFv genes. Suitable expression systems can include bacterial expression systems, mammalian expression systems, yeast expression systems, insect cell expression systems, plant cell expression systems and the like. Expression systems, for example, can be E. coli expression systems, CHO cell expression systems, and the like.

In one embodiment, the $V_H$ amino acid sequences and $V_L$ amino acid sequences are expressed as a recombinant scFv polypeptide. The scFv polypeptide is encoded by a corresponding scFv gene that can include DNA encoding a $V_H$ amino acid sequence and also can include DNA encoding $V_L$ amino acid sequence (148). The scFv gene may also include DNA that encodes linker sequences. The linker sequences can include peptides between the $V_H$ amino acid sequence and $V_L$ amino acid sequence. The linker sequences can be between about 3 amino acids and about 30 amino acids. Linker peptides outside of this range may also be included. The linker peptide can be rich in glycine for flexibility and/or serine or threonine for solubility and can either connect the N-terminus of the variable heavy chain and the C-terminus of the variable light chain, or vice versa. In one embodiment, the linker peptide is a 17 amino acid sequence including serine and glycine as shown, for example, in SEQ ID NO:15 from amino acid 122 to amino acid 138. Other sizes and combinations of amino acids are also within the scope of this description.

Figure 8:
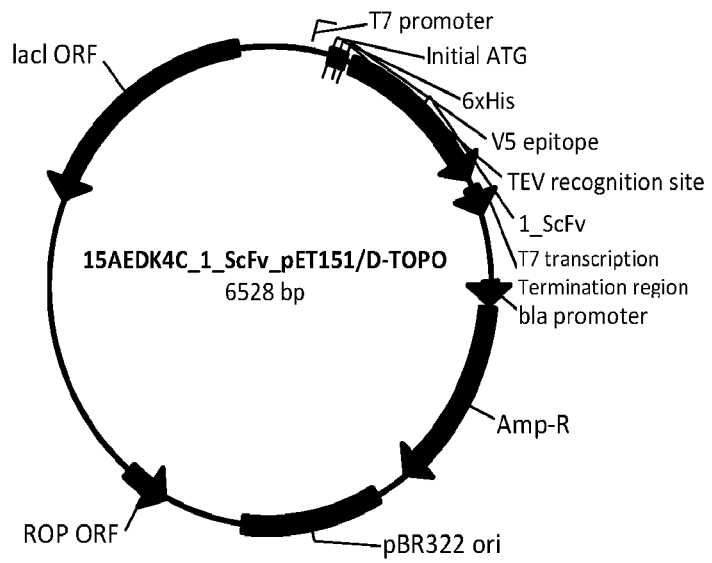
FIG. 8 is a diagram of one of 21 GeneArt pET151 plasmids containing an scFv gene; (CI81_1 is represented).

In one embodiment, the scFv gene is inserted into an expression plasmid for expression in E. coli, e.g. pET151 plasmid (156) as shown in FIG. 8. Other suitable plasmids for expression in E. coli may be used and are within the scope of this description.

The $V_H$ amino acid sequences and $V_L$ amino acid sequences can be expressed as a rmAb. The rmAb can be encoded by a corresponding gene or genes that can include DNA encoding a $V_H$ amino acid sequence, DNA encoding $V_L$ amino acid sequence and DNA encoding the constant regions of a monoclonal antibody. In addition, DNA encoding the hinge region and the unique-to-chicken $4^{th}$ constant region (CH4) may also be included. The rmAb may have one, two, three and/or four of the constant regions of the chicken antibodies included in the rmAb. Since neutralization occurs by passive immunity, the constant region (Fc) is optional and may or may not be included.

In one embodiment, the candidate antibody gene sequences can be synthesized and TOPO®-directionally inserted into T7-regulated bacterial expression plasmids. In other embodiments, mammalian expression systems with a cytomegalovirus promoter can be used. Other expression plasmids may also be used and all are within the scope of this disclosure.

The recombinant polypeptide may be glycosylated when expressed in recombinant expression system. The glycosylation of the recombinant polypeptides can vary and can be dependent on the specific expression system utilized. In one embodiment, the glycosylation of the recombinant polypeptide can be, for example, based on the glycosylation in CHO expression system. Other suitable glycosylation can also be part of the recombinant polypeptide. Recombinant polypeptides may or may not include the same glycosylation profile as the glycosylation profile in the naturally occurring antibodies purified from birds. In other words, the antibodies purified from birds may have a different glycosylation profile than the glycosylation profile of the recombinant polypeptides expressed in expression systems. Recombinant polypeptides without any glycosylation, e.g. aglycosylated recombinant polypeptides, are also within the scope of this invention.

Expression of the scFv polypeptides or binding domains can be constitutive or inducible. In one embodiment, the expression of scFv polypeptides is induced during the final hours of growth.

In some embodiments, expression of the scFv polypeptides may result in the binding domain folding properly to bind an antigen. In some embodiments, the expression of the recombinant scFv polypeptide may need further processing prior to formation of a functional binding domain. Processing of the polypeptide can lead to successful protein folding resulting in binding of the antigen. In one embodiment, the expression of the scFv polypeptide can form inclusion bodies. The scFv polypeptide may be solubilized and refolded (160) for successful protein folding resulting in antigen binding. In one embodiment, refolding the protein may result in changes in disulfide bond formation that can lead to formation of functional binding domains. Other methods to process the recombinant polypeptides into an active state may also be used.

The recombinant polypeptides expressed, e.g. scFv polypeptides or rmAb, can be screened (164) for antigen binding and specificity. Any suitable antigen specificity screening protocols may be used and all are within the scope of this disclosure. In one embodiment, an indirect ELISA screening assay is used as described below in the Examples. In another embodiment, a phage display library screening may be used.

The recombinant polypeptides that have specificity for the antigen can be identified. Recombinant polypeptides that include the functional binding domains that have specificity for the antigens can be included in the therapeutic compositions described herein.

The present description can also include methods for preventing disease in an animal. The method can include hyperimmunizing a bird, e.g. a chicken, with one or more disease antigens. Samples from the bird are obtained at a pre-HI immunological time point and at a post-HI immunological time point as described above. Using the methods described herein, recombinant polypeptides, e.g. scFv polypeptides and/or rmAbs, can be identified, expressed in an expression system and screened for binding and/or neutralizing the one or more disease antigens. Candidate recombinant polypeptides that can bind and/or neutralize the disease antigens can be included in therapeutic compositions and administered to the animal for prevention of disease.

In one embodiment, the method can include hyperimmunizing birds with antigens from *Mannheimia haemolytica*. In some embodiments, the antigen may be the outer membrane protein, leukotoxin or combinations thereof. The recombinant polypeptides with functional binding domains that have specificity for the antigens from *Mannheimia haemolytica* can be included in the therapeutic compositions for preventing diseases associated with *Mannheimia haemolytica*.

The present description can also include a method for generating specific recombinant polypeptides that can bind and/or neutralize an antigen of interest in an in vitro expression system. This can result in the production of large amounts of the recombinant polypeptides that are specific to an antigen(s) of interest and can be included in therapeutic compositions. The method can include administering one or more disease antigens to a bird and identifying the amino acid sequences of the variable light chain and variable heavy chains of the antibody repertoire generated in the hyperimmunized state of a bird. Candidate amino acid sequences can be identified for the variable light chain and variable heavy chain sequences. Recombinant DNA molecules can be synthesized that encode at least these portions of the variable light chains and variable heavy chain regions. The recombinant DNA molecules can also include DNA encoding linker peptide sequences, constant regions of the antibody molecules or other amino acid sequences for generating a functional binding domain. The recombinant DNA molecules can be expressed in an in vitro expression system as described herein and screened for specificity to the initial antigen of interest. Recombinant polypeptides that can bind the antigen of interest in a screening assay can be identified and used in expression systems to generate large quantities. Identification, expression and purification of these recombinant polypeptides specific for an antigen of interest results is advantageous for use in therapeutic compositions with considerable cost savings.

The present description also includes compositions. The compositions can be therapeutic compositions that can include recombinant polypeptides. The recombinant polypeptides can be scFv polypeptides, rmAb polypeptides and the like. The recombinant polypeptides can include a functional binding domain for binding and/or neutralizing an antigen. The binding domains are recombinant products that encompass all of the recombinant polypeptide or a portion of the recombinant polypeptide. The binding domains can be part of or all of the scFv polypeptides. The binding domain can be part of an rmAb. In other words, scFv polypeptides and rmAbs can include the amino acid sequences necessary to form a binding domain of an antigen. The scFvs or rmAbs, once expressed, can include a functional binding domain that can bind and/or neutralize an antigen when expressed in expression systems. This can result in compositions of potently neutralizing antibodies through recombinant protein expression.

The binding domain of the recombinant polypeptide can include amino acid sequences from the variable light chain domain and amino acid sequences from the variable heavy chain domain. The binding domain of the recombinant polypeptide can bind and/or neutralize an antigen. In some embodiments, the antigen that the binding domain binds and/or neutralizes after expression and successful folding is the same antigen or epitope that was initially used to hyperimmunize birds for identifying the amino acid sequences of the binding domain.

In one embodiment, the antigen is the same or similar to the antigen used to hyperimmunize birds. The binding domains of the polypeptides can include amino acid sequences from variable regions of a heavy chain immunoglobulin molecule and amino acid sequences from variable regions of a light chain immunoglobulin molecule. The amino acid sequences of the variable regions of the light chain and the heavy chain can be determined based on the antibody repertoire generated due to the hyperimmunization of the bird and the analysis of the resultant mRNA levels in the serum of the hyperimmunized bird. The variable regions of the heavy and light chains can be part of a single-chain variable fragment (scFv) polypeptide and/or they can be part of a recombinant monoclonal antibody (rmAb).

The recombinant polypeptides in the therapeutic compositions may be generated in a bacterial expression system, a mammalian expression system and the like. In one embodiment, the therapeutic composition may include a single recombinant polypeptide. In another embodiment, the therapeutic composition may include two or more recombinant polypeptides. The two or more polypeptides may be directed to the same antigen but have different specificities. The recombinant polypeptides in the composition may be directed to different disease antigens.

The recombinant polypeptides can be characterized. The characterization can be used to identify the specific recombinant polypeptides that may be used alone or in combinations in a therapeutic composition. The precise epitope and effect of neutralization by the recombinant polypeptides can be determined. The recombinant polypeptides can be characterized by locating binding sites on the antigen, quantifying binding affinities and the stability of rmAbs, optimized expression of scFvs or whole IgG with relevant glycosylation profiles or any confirmation of lab engineered rmAbs including but not limited to: nanobody, diabody, tribody and the like.

In one embodiment, the recombinant polypeptide may be aglycosylated. In other embodiments, the recombinant polypeptides may have glycosylation profiles that are different than the glycosylation profile of antibodies that are naturally occurring in the birds, e.g. chicken antibodies. The rmAbs may also be conjugated with other molecules to act as delivery vehicles for biomolecules or chemicals. In one embodiment, biconjugation with an antibody can be used as prodrug therapy, antibody-directed enzyme prodrug therapy (ADEPT), where an inactive antibiotic is first given (prodrug) and only when it can interact with the conjugated Ab does it become active and lethal to bacteria. The Ab can be bound to the specific pathogen and confer pathogen-specific antibiotic targeting.

In one embodiment, the therapeutic compositions can include recombinant scFv polypeptides against the antigens leukotoxin and/or OMP. The therapeutic compositions can include any scFv polypeptides that bind and/or neutralize the leukotoxin and/or the OMP.

In some embodiments, the therapeutic compositions can include the scFv polypeptides of SEQ ID NO:15, SEQ ID NO:17, SEQ ID NO:18, SEQ ID NO:19, SEQ ID NO:20, SEQ ID NO:21, SEQ ID NO:23, SEQ ID NO:25, SEQ ID NO:26, SEQ ID NO:28, SEQ ID NO:29, SEQ ID NO:30, SEQ ID NO:31, SEQ ID NO:32, SEQ ID NO:33, SEQ ID NO:34 or combinations thereof.

The therapeutic composition can also include additives, carriers and the like in order to improve the utility of the composition during or after administration to an animal.

The therapeutic compositions may be administered to animals including humans and other mammals. The composition may be administered to agriculture animals such as cattle, swine, poultry and the like.

The present description also includes compositions that include the recombinant DNA molecules that encode the recombinant polypeptides described herein. In one embodiment, the present description includes the recombinant DNA molecule illustrated in FIG. 5.

EXAMPLES

Example 1

Materials and Methods

Chickens. Eighteen White Bovans, approximately 26 weeks old, were enrolled and individually caged with colored leg bands for identifying the five study groups. There were three hens in each of the five study groups, one group of two hens acted as the adjuvant control, and one hen received no injections and served as a blood collection method control. Three of the five groups received three different concentrations of the immunogen. Vaccination histories included 13 immunizations, for the health of the bird, and included vaccines for both viral and bacterial avian pathogens. Traceable eggs, to be used for confirmation of immunogen efficacy and charting immune response curves over time, were hand-collected and the date of collection was recorded by marker on the egg shell.

Hyperimmunization and blood collection. The outer membrane protein (OMP) and leukotoxin from *Mannheimia haemolytica* were used. The vaccine (Nuplura) was used and included OMP purified from bacterial cultures and recombinant leukotoxin obtained from Novartis Animal Health US Inc. Larchwood, Iowa. The vaccine was diluted in combination with sterile-filtered PBS and the adjuvant Emulsigen-D was used purchased from MVP Laboratories, Omaha, Nebr. Three immunogen concentrations were formed: 1×, 5×, and 10×; based on manufacturer's dosing recommendations of 22 µl per kilogram of body weight. Prior to injections, the non-immune repertoire was sampled from venous blood collected by wing bleeds from all hens. The volume of blood collected varied, but a constant 1.0 ml collected for total RNA extraction into lithium heparin (BD) anticoagulated tubes, while the remainder allowed to clot and was saved for serum collection. Hens were hyperimmunized by 1.0 ml intramuscular injections (IM). Adjuvant control hens received identical 1.0 ml diluted adjuvant only, IM. Seven days following the primary, a boost was delivered in an identical manner as the primary IM injections. Thirteen days following the primary hyperimmunization, the post-state repertoire was sampled from venous blood collected from all hens in the second wing vein. Blood samples for both immunological time points were transported back to the laboratory on ice for same-day processing.

Sample processing and RNA extractions. Performed twice for the non-immune and hyperimmunized collections, PBMCs were isolated from anticoagulated blood by density gradient centrifugation (Lymphoprep gradient and SepMate columns, StemCell Technologies, Vancouver, BC, Canada). Blood samples were first diluted 1:2 in PBS+2% fetal bovine serum (FBS), then added to the gradient solution, which has a specific density for PBMCs. Using the specialized centrifuge columns, samples were centrifuged at 1200×g for 10 minutes at room temperature. Supernatant, containing PBMCs, was decanted and washed once using the PBS+FBS solution. Cells were collected by centrifugation at 300×g for 8 minutes at room temperature.

mRNA isolation. Isolated PBMCs were then immediately extracted using the mirVana kit (Ambion™) purchased from ThermoFisher Scientific in Waltham, Mass. as described below and the total nucleic acid was stored at −75° C. Serum was also collected, from the clotted blood samples after centrifugation, and stored at −20° C.

Immediately following PBMC enrichment, cell pellets were lysed using 600 uL of mirVana Lysis Buffer and 60 uL miRNA Homogenate Additive (kit provided). Samples were fully suspended by vortexing followed by a 10 minute incubation on ice. Sets of eight sample mRNAs were isolated at a time, in a randomized order, using mRNA Direct Dynabeads (Ambion™) purchased from ThermoFisher Scientific in Waltham, Mass. The purification kit isolates mRNA by their poly(A) tails.

Next, 600 uL of Acid-Phenol:Chloroform (kit provided) was added to denature unwanted DNA and keep RNA in an aqueous state. Samples were vortexed for 1 minute. To separate aqueous and organic layers, samples were then centrifuged at 18,000×g for 5 min at room temperature. The aqueous (upper) layer, containing the RNA, was collected and sample volumes were recorded. Next, 1.25 times the sample volume of 200-proof ethanol was added to precipitate RNA and samples were again mixed by vortexing. Kit-supplied centrifugation columns were loaded with samples and RNA was bound to the column matrix by centrifugation at 10,000×g for 15 seconds at room temperature. Multiple spins to bind RNA were necessary since columns hold only 700 uL. Sample portion that flowed through the column into a collection tube was discarded and bound sample RNA was washed to remove protein using 700 uL miRNA Wash 1. Keeping the centrifugation speed the same, columns were spun for 10 seconds. Flow-through fraction was again discarded. Sample RNA was washed twice with 500 uL kit-provided Wash 2/3 Solution and the same portion was discarded. To minimize Wash Solution carryover, sample columns were dried by centrifugation for 1 min. Using sterile and nuclease-free collection tubes, 100 uL of 95° C.-heated Elution Buffer was added to sample columns to release sample RNA. Extraction products were collected through centrifugation for 30 seconds. Samples of RNA were stored at −80° C.

mRNA Enrichment Protocol and Reverse Transcription

Sample RNA stored at −80° C. was thawed on ice for 1 hour. The samples were enriched for mRNA using Ambion™ mRNA Direct Dynabeads kit purchased from ThermoFisher Scientific in Waltham, Mass.). 132 uL of Magnetic beads were added to a 1.5 mL microcentrifuge tube and placed in a magnetic tube rack and allowed to pellet on the side of the centrifuge tube. Pipetted and discarded the storage solution. Tubes were removed from magnetic rack and suspended beads in 132 uL kit-provided Lysis/Binding Buffer. Next, 150 uL of Lysis/Binding buffer was added to thawed sample RNA. 30 uL of resuspended magnetic bead mixture was added to each microcentrifuge tube containing the diluted sample RNA. A five minute benchtop incubation allowed for the capture of polyadenylated RNA. To begin the washing steps, microcentrifuge tubes were loaded into the magnetic rack and supernatant was pipetted and discarded when the solution had cleared. Microcentrifuge tubes were removed from the magnetic rack and mRNA-bound magnetic beads were washed using 200 uL kit-provided Wash Solution A. Beads were suspended by gentle pipetting and then recollected in the magnetic rack. Supernatant was removed by pipetting and the samples were washed once more with Wash Solution A. Following the same process, samples were washed with 300 uL kit-provided Wash Solution B. Supernatant from each wash was discarded. To temporarily release the enriched sample mRNA, 50 uL of 80° C.-heated nuclease-free water was added and incubated on the benchtop for 30 seconds. Next, mRNA was recaptured onto the magnetic beads through the addition of 50 uL Lysis/Binding Buffer. Samples were incubated on the benchtop for 5 minutes. Repeated the two Wash Solution steps to further purify sample mRNA. To release mRNA for the second and final time, 10 uL of 80° C.-heated nuclease-free water was added and incubated on the benchtop for 30 seconds. Microcentrifuge tubes were placed in the magnetic rack and enriched sample mRNA was collected by a pipette and stored on ice.

Because cDNA is more tolerant to freeze/thaw cycles than mRNA, isolated mRNA was immediately reverse-transcribed using a RT enzyme Superscript III/VILO, Invitrogen kit purchased from ThermoFisher Scientific in Waltham, Mass.

The cDNA from the reverse transcription was stored at −20° C. The 20 µl RT reaction volumes were comprised of: 4 µl 5×VILO reagent, 2 µl 10×Superscript reagent, 10 µl PCR-grade water, and 4 µl sample mRNA. The thermocycler was programmed for: 25° C. for 10 min, 42° C. for 60 min, 85° C. for 5 min, and a 4° C. temperature hold.

Sample cDNA was purified from reverse transcription enzymes and primer oligonucleotides by using AMPure XP magnetic bead purification kit purchased for Agencourt/Beckman Coulter in Indianapolis, Ind. Sample cDNA was purified by adding 1.8×sample volume of AMPure magnetic beads. Mixture was incubated on the benchtop for 5 minutes. Bead mixture in the microcentrifuge tube was placed in the magnetic rack and, after clearing, supernatant was removed by pipetting and discarded. Leaving the microcentrifuge tubes in the magnetic rack, captured cDNA on the beads were washed using 30 uL freshly-prepared 70% ethanol. Following a 30 second incubation, wash solution was removed by pipette and discarded. Repeated the wash step twice. After removing the second wash, beads were dried to minimize ethanol contamination for 4 minutes on the benchtop. To release sample cDNA, microcentrifuge tubes were removed from the magnetic rack and 20 uL of Low TE Buffer was added and vortexed. Microcentrifuge tubes were once again placed in the magnetic rack and supernatant containing the purified sample was collected by pipette. Purified cDNA was stored at −20° C. until $V_H$ and $V_L$ gene amplification.

Amplification of $V_L$ and $V_H$ genes. From the 18 enrolled chickens, six were randomly selected for amplification and sequencing. Of the selected six, one being mandated to be an adjuvant control hen, the randomization resulted in the selection of two 10×, two 1×, and one 5× immunogen concentrations. The $V_L$ primers (FWD: AACCGTCAAGAT-CACCTGCTCC (SEQ ID NO:1), REV: GGTTGTCCCGGCCCCAAA (SEQ ID NO:2)) and $V_H$ primers (FWD: TCTGCAAGGCCTCCGGGTT (SEQ ID NO:3), REV: TTCGGTCCCGTGGCCCCA (SEQ ID NO:4)) were both designed to lay down in the end of the framework 1 region and amplify across the three CDRS to the start of framework 4 (FIG. 2). The light chain primers were designed using Genbank accession number M33049 as a $V_L$ gene reference and produced a theoretical product length of 265 base pairs. The heavy chain primers were designed from Genbank accession number D70821, and would produce an amplicon with a theoretical length of 296 bp. These amplicon sizes were used as a rough estimation of product formation, since the CDR hypervariable regions impart variability in product sizes, as seen in gel products and histograms in FIGS. 3 and 4. The 20 µl amplifying PCR reactions consisted of: 10 µl master mix (AccuStart PCR Supermix, Quanta Biosciences, Beverly, Mass.), 6 µl PCR-grade water, 2 µl of $V_L$ or $V_H$ primers at a final concentration of 500 nmoles each (synthesized by IDT), and 2 µl sample cDNA. The thermocycler program was: 94° C. 2 min; 30 cycles of 94° C. for 30 sec, 60° C. for 1 min, and 72° C. for 1 min; and a 4° C. temperature hold. Samples of the $V_L$ and $V_H$ amplicons were run out on agarose gels to confirm the correct product size (FIG. 2). Amplicons were purified using AMPure XP magnetic beads (Agencourt/Beckman Coulter) and suspended in 30 µl PCR-grade water.

Figure 3:
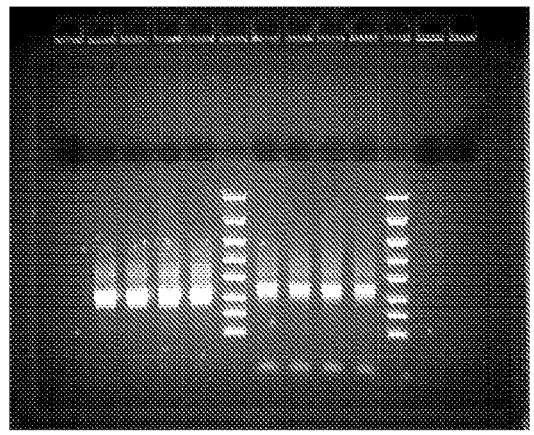
FIG. 3 is a photograph of a gel with immunoglobulin variable light (lanes 2-5) and heavy (lanes 7-10) chain amplicons prior to AMPure bead purification and DNA sequencing library preparation.

FIG. 3 is a photograph of a gel that shows the results of the amplification. In FIG. 3, immunoglobulin variable light (lanes 2-5) and heavy (lanes 7-10) chain amplicons are shown prior to AMPure bead purification and DNA sequencing library preparation. PCR amplifications run in duplicate, with Non-immune samples in lanes 2 and 3, and, 7 and 8. Post-hyperimmunized samples are in lanes 4 and 5, and, 9 and 10. DNA ladders (lanes 6 and 11) from the bottom of the gel to the top: 100 bp, 200, 300, 500, 800, 1250, 2000, and 4000 bp.

Sequence library preparation and Ion Torrent sequencing. Purified $V_L$ and $V_H$ amplicons were quantified using a Qubit 2.0 fluorometer (dsDNA HS assay, Invitrogen, ThermoFisher Scientific in Waltham, Mass.).

A total of 24 libraries for the six chickens were prepared—each $V_L$ or $V_H$ amplification before and after hyperimmunization. To prepare the libraries, Ion Torrent's Ion Plus Library Preparation Kit were used purchased from Ion Torrent, Thermo Fisher, Carlsbad, Calif. Diluted samples in nuclease-free water to a sample input amount ranging between 45 ng and 95 ng. Maximizing sample input negated the need to amplify libraries, which introduces PCR-based errors. Total volume equaled 79 uL. Next, 20 uL 5× End Repair Enzyme and luL End Repair Enzyme (both kit provided) were added to samples, mixed by pipetting, and incubated on the benchtop for 20 minutes. After the ends of sample DNA had been repaired and ready for ligation, samples were purified by AMPure XP magnetic beads: A). Pipetted 180 uL bead solution (1.8 times the sample volume), mixed by pipetting 5 times, and incubated on the benchtop for 5 minutes. B). Placed microcentrifuge tubes in a magnetic rack and allowed beads to pellet for 3 minutes. Keeping tubes in the rack, supernatant was removed by pipette and 500 uL 70% ethanol (freshly prepared) was used to wash DNA-loaded beads. Repeated for a total of 2 washes. C). After removing the second wash, beads were dried to minimize ethanol contamination for 4 minutes on the benchtop. D). To release samples, microcentrifuge tubes were removed from the magnetic rack and 25 uL of Low TE Buffer (kit provided) was added and vortexed. E). Microcentrifuge tubes were once again placed in the magnetic rack and supernatant containing the purified sample was collected by pipette.

Matching non-immune and immunized repertoire samples' $V_L$ and $V_H$ concentrations, amplicon input amounts varied between 45-95 ng (within the accepted range of 10-100 ng) as allowed by the library protocol. Amplicon libraries received unique sequencing barcodes allowing two libraries to be sequenced on one Ion 316v2 BC chip. To ligate adapters and barcode oligonucleotides to sample amplicons, the following were added to 0.2 mL PCR microcentrifuge tubes in the following order: 25 uL purified sample DNA, 10 uL 10× Ligase Buffer, 2 uL Ion P1 Adapter, 2 uL Xpress Barcode, 2 uL dNTP Mix, 49 uL nuclease-free water, 2 uL DNA Ligase, and 8 uL Nick Repair Polymerase. Sample mixtures were loaded in a thermocycler and the following cycle was run: 25° C. 15 minutes, 72° C. 5 minutes, and a 4° C. hold. Processed sample libraries were purified for a second time using AMPure XP magnetic beads and eluted in 20 uL Low TE Buffer. Libraries stored at −20° C.

Ion Universal Library Quantification

Libraries were quantified by PCR (Universal Library Quantitation Kit, Ion Torrent™ ThermoFisher Scientific, Carlsbad, Calif.) and diluted in TE buffer to a concentration of 40 pM. Sample libraries were quantified by real time PCR prior to Ion Chef™ Ion Sphere Particle, (ISP) templating. Ion Chef™ ISP templating is a process in semiconductor sequencing, where a bead (ISP) captures one library read (one sequence theoretically). Through emulsion PCR to amplify that one read in a compartmentalized environment, the surface of the bead (ISP) is covered, or templated, with a monoclonal and singular ligated amplicon. Libraries were loaded in the Ion Chef™, an automated library templating and chip-loading platform. After an overnight emulsion PCR program in the Ion Chef, the two loaded chips were sequenced, one per day, while the other was kept at 4° C. As with all the previous selection events, the sequencing order of the two chips was randomized. PCR reactions included the following: 1 uL Primer/probe, 10 uL Master Mix, 4 uL nuclease-free water, and 5 uL sample library diluted $2 \times 10^{-3}$ in water. Kit standards were diluted 1:10 in nuclease-free water to establish a five-point standard curve starting at 6.8 pM and ending at $6.8 \times 10^{-4}$ pM. Sample and standard reactions were loaded into a thermocycler and the following cycle program was run: 50° C. 2 minutes, 95° C. 20 seconds, and 40 cycles of 95° C. 1 second and 60° C. 20 seconds.

Following the PCR assay, library concentrations were calculated using the standard curve linear equation and accounting for the sample dilution factor. Libraries were diluted to 40 pM concentrations, in Low TE Buffer, and pooled pairwise as input into the Ion Chef automated templating system. Following the overnight Ion Chef preparation, one of the two loaded 316v2 BC sequencing chips was sequenced that day. The remaining chip was kept at 4° C. and sequenced the following day.

Sequencing statistics and details are summarized in Table 1.

TABLE 1

| | | | | | Nucleotides | | | |
| --- | --- | --- | --- | --- | --- | --- | --- | --- |
| | | | | | | | | Inclusion Criteria 2 |
| | | | | | | Inclusion Criteria 1 | | Reads between |
| Chicken ID | Barcode | Assignment | Ion Chip loading | ISP clonality | Barcoded Reads | Reads with fwd primer | Reads with rev primer | Reads with both primers | 200bp and 450bp |
| Green (HI) | 1 | non-immune $V_L$ | 85% | 64% | 1,174,882 | 452,064 | 58,589 | 53,881 | 53,257 |
| | 2 | immunized $V_L$ | | | 1,597,935 | 683,709 | 88,165 | 82,152 | 81,100 |
| | 3 | non-immune $V_H$ | 79% | 74% | 1,881,348 | 1,021,036 | 148,049 | 142,234 | 141,405 |
| | 4 | immunized $V_H$ | | | 1,253,992 | 693,484 | 333,335 | 316,346 | 315,142 |

TABLE 1-continued

| | | | Ion Chip loading | ISP clonality | | | | | |
|---|---|---|---|---|---|---|---|---|---|
| Black/Red (HI) | 5 | non-immune $V_L$ | 85% | 64% | 1,125,718 | 587,453 | 124,344 | 118,266 | 116,919 |
| | 6 | immunized $V_L$ | | | 1,898,071 | 849,609 | 184,531 | 173,327 | 171,569 |
| | 7* | non-immune $V_H$ | 91% | 75% | 4,084,192* | 2,273,362 | 486,462 | 456,733 | 452,692 |
| | 8* | immunized $V_H$ | 90% | 71% | 3,778,522* | 2,209,264 | 211,457 | 194,392 | 182,241 |
| Yellow (HI) | 9 | non-immune $V_L$ | 92% | 71% | 2,663,011 | 1,238,784 | 138,741 | 131,611 | 130,355 |
| | 10 | immunized $V_L$ | | | 866,009 | 422,564 | 60,299 | 57,220 | 56,691 |
| | 11 | non-immune $V_H$ | 91% | 68% | 1,768,143 | 1,005,070 | 228,405 | 215,291 | 213,724 |
| | 12 | immunized $V_H$ | | | 1,476,694 | 778,913 | 192,839 | 183,024 | 181,855 |
| Blue (HI) | 13 | non-immune $V_L$ | 88% | 73% | 1,751,682 | 826,748 | 68,497 | 64,773 | 64,008 |
| | 14 | immunized $V_L$ | | | 1,718,861 | 807,934 | 70,729 | 67,628 | 66,801 |
| | 15 | non-immune $V_H$ | 94% | 69% | 1,924,087 | 1,085,642 | 240,598 | 231,625 | 230,407 |
| | 16 | immunized $V_H$ | | | 1,666,537 | 956,727 | 208,507 | 197,764 | 196,263 |
| Yellow/White (HI) | 17 | non-immune $V_L$ | 88% | 76% | 1,031,682 | 443,541 | 139,642 | 131,262 | 130,219 |
| | 18 | immunized $V_L$ | | | 2,747,195 | 1,288,696 | 381,450 | 361,707 | 359,136 |
| | 19 | non-immune $V_H$ | 91% | 75% | 1,927,656 | 1,081,595 | 306,582 | 294,428 | 293,102 |
| | 20 | immunized $V_H$ | | | 1,868,625 | 1,053,350 | 262,553 | 248,998 | 247,562 |
| Yellow/Black (adjuvant control) | 21 | non-immune $V_L$ | 90% | 68% | 1,438,226 | 710,225 | 199,483 | 190,783 | 189,021 |
| | 22 | immunized $V_L$ | | | 1,991,610 | 941,121 | 275,386 | 261,391 | 259,371 |
| | 23 | non-immune $V_H$ | 87% | 77% | 1,803,074 | 1,032,044 | 196,231 | 187,124 | 183,991 |
| | 24 | immunized $V_H$ | | | 1,804,181 | 1,076,754 | 202,091 | 186,642 | 183,731 |

| | | | | | Amino Acids Inclusion Criteria 3-5 | | |
|---|---|---|---|---|---|---|---|
| Chicken ID | | Barcode | Ion Chip loading | ISP clonality | Reads in correct frame | Reads without a stop codon | Reads with correct CDR3 motif |
| Green (HI) | | 1 | 85% | 64% | 23,197 | 18,429 | 16,922 |
| | | 2 | | | 35,921 | 28,047 | 25,606 |
| | | 3 | 79% | 74% | 47,127 | 15,950 | 14,134 |
| | | 4 | | | 107,813 | 42,613 | 38,730 |
| Black/Red (HI) | | 5 | 85% | 64% | 59,309 | 51,146 | 48,377 |
| | | 6 | | | 90,185 | 77,632 | 73,338 |
| | | 7* | 91% | 75% | 148,254 | 49,823 | 42,833 |
| | | 8* | 90% | 71% | 61,000 | 20,500 | 17,417 |
| Yellow (HI) | | 9 | 92% | 71% | 45,000 | 33,555 | 30,575 |
| | | 10 | | | 20,209 | 15,208 | 13,957 |
| | | 11 | 91% | 68% | 79,432 | 34,338 | 30,574 |
| | | 12 | | | 68,070 | 31,476 | 28,421 |
| Blue (HI) | | 13 | 88% | 73% | 16,910 | 11,316 | 9,495 |
| | | 14 | | | 19,469 | 13,550 | 11,583 |
| | | 15 | 94% | 69% | 80,230 | 32,314 | 29,859 |
| | | 16 | | | 69,020 | 30,367 | 28,310 |
| Yellow/White (HI) | | 17 | 88% | 76% | 81,791 | 74,371 | 71,444 |
| | | 18 | | | 217,602 | 195,860 | 187,711 |
| | | 19 | 91% | 75% | 100,389 | 45,433 | 41,642 |
| | | 20 | | | 83,252 | 36,206 | 32,726 |
| Yellow/Black (adjuvant control) | | 21 | 90% | 68% | 104,536 | 91,232 | 87,395 |
| | | 22 | | | 146,241 | 128,604 | 123,322 |
| | | 23 | 87% | 77% | 63,893 | 24,916 | 22,590 |
| | | 24 | | | 63,748 | 23,779 | 21,257 |

Figure 4A:
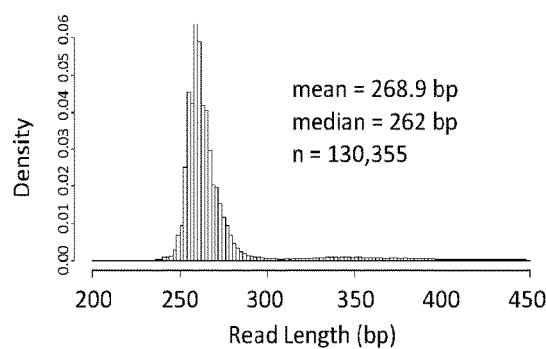
FIGS. 4A-4D are plots of read length histograms after DNA sequencing for the samples in FIG. 3.
Figure 4B:
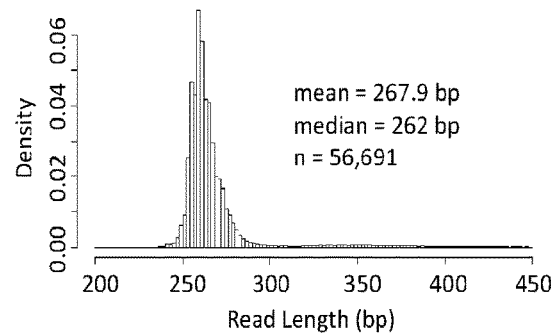
Figure 4C:
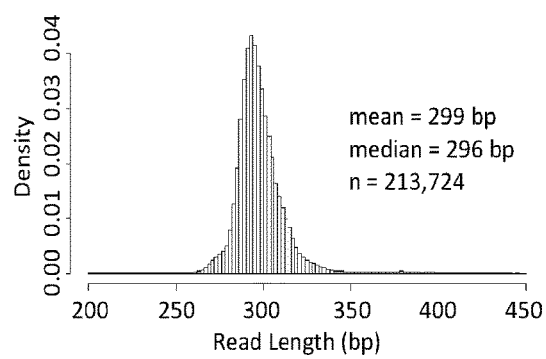
Figure 4D:
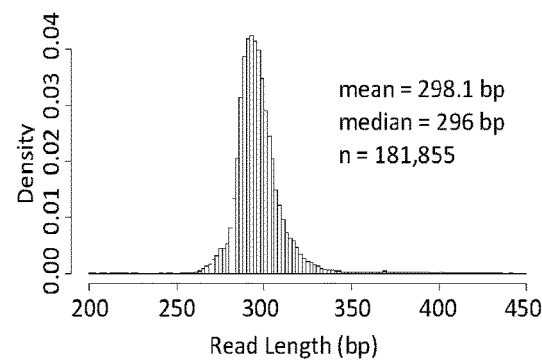

In FIGS. 4A-4D, read length histograms are shown following DNA sequencing for the agarose gel samples in FIG. 3. FIG. 4A is $V_L$ Non-immune state; FIG. 4B is $V_L$ Post-hyperimmunized state; FIG. 4C is $V_H$ Non-immune state; FIG. 4D is $V_H$ Post-hyperimmunized state. The theoretical means during primer design were 265 bp for $V_L$ and 296 bp for $V_H$.

In FIGS. 5A-5D, CDR3 read length distributions of the top 5% most abundant repertoire sequences for one chicken are shown. Although the shape of the paired distributions does not look significantly different, the ranked order by abundance of CDRH3 lengths was significantly different by a paired t-test (corrected p-value=0.03168).

Bioinformatic analysis. Total, unfiltered reads were processed from tabular files formatted from Ion Torrent fastq files. Working in RStudio, two inclusion criteria were applied to include reads that contained primer sequence and were of a size between 200 and 450 bp and to nucleotide reads that reduced a study average number of reads from $2.01 \times 10^6$ (SD=$9.11 \times 10^5$) to $2.03 \times 10^5$ (SD=$1.38 \times 10^5$). Included reads were then translated to their amino acid sequences where a third and fourth inclusion criteria further selected reads that had no stop codons and were in the correct reading frame. A fifth and final inclusion event involved implementing a motif search using ScanProSite, for CDRH3 (D-x(1,5)-[YF]-[YF]-C-x(1,75)-WGHGT) and CDRL3 (D-x(1,10)-[YF]-C-x(1,30)-FGAGTT). This tool not only selected for reads of interest, but indexed the CDR3 regions from reads. Further motif filtration yielded CDR3s defined as being the sequence of residues between the N-terminus Cys and the C-terminus Trp/Phe. The resulting indexed CDR3s were clustered using the CD-HIT webserver at 95% similarity for the CDRH3s and 90% for the shorter CDRL3s. Regardless of 95 or 90%, this allowed for one mismatch for the majority of CDR3s. Twelve data frames of CD-HIT results were then created: six $V_L$ and six $V_H$. Shifts or changes in antibody frequencies between immune states for each CDR3 cluster were calculated and represented by the term Δfrequency.

Figure 6A:
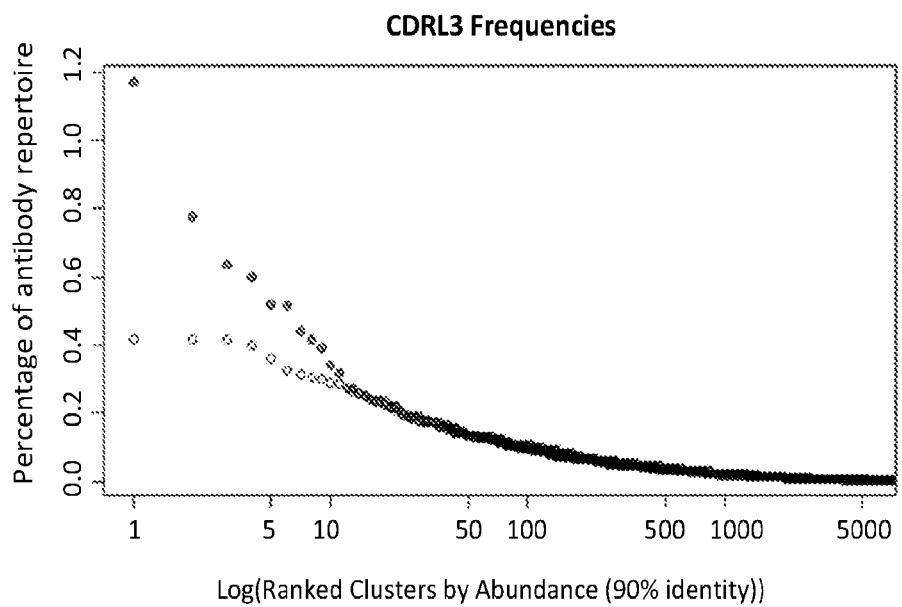
FIGS. 6A and 6B are plots of repertoire frequency distributions resulting from CD-HIT clusters for one chicken. Non-immune state sample (white) and Post-hyperimmunized (gray).
Figure 6B:
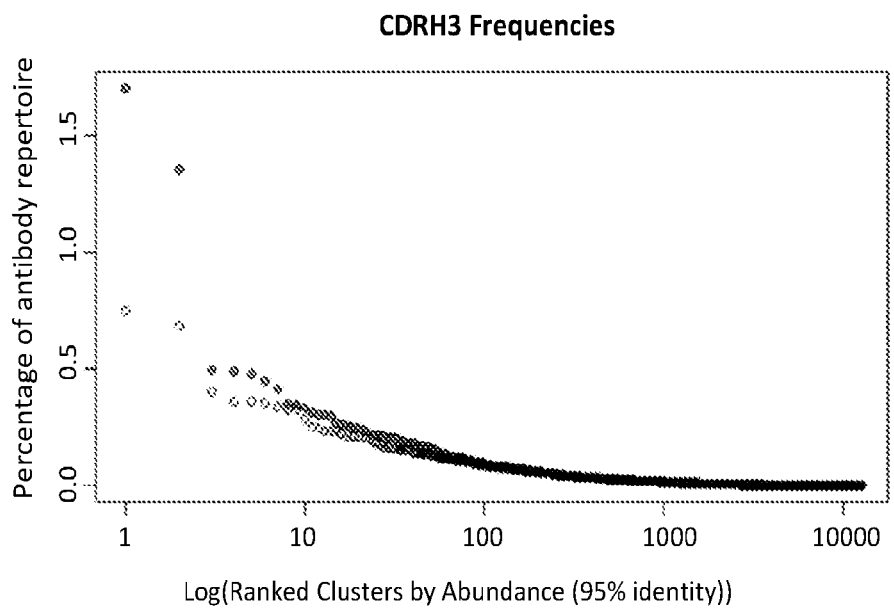

In FIGS. 6A-6B, repertoire frequency distributions are shown resulting from CD-HIT clusters for one chicken. Non-immune state sample (white) and Post-hyperimmunized (gray).

Candidate $V_H$ sequence selection. Using a custom, ad-hoc three-conditional ruleset, candidate antibody sequences were selected for further analysis. Ruleset parameters included the following dataset attributes: a minimum Hyperimmunized Frequency, a maximum Non-immune Frequency, and a minimum delta frequency. The objective of the ruleset was to select candidate antigen-specific CDRH3 sequences in a non-biased and high-throughput compatible manner. Success of the ruleset would be measured as not including Adjuvant-only control sequences. Applying the ruleset to a consolidated dataset of 82,000 sequences from all six chickens, the following conditions selected 14 candidates: a Hyperimmunized Frequency greater than 0.4%; a Non-immune Frequency of less than 0.2%; and a delta frequency greater than 30.

Ruleset R Code:
c=df[df$Immunized.Frequency>0.004 &
df$Corresponding.Nonimmune.Frequency<0.002 &
df$Delta.Frequency>30, 'ID']

Pairing $V_L$ sequences with candidates. Abundant CDRL3 sequences were matched to the candidate $V_H$ sequences by relative rank orders from immunized repertoires.

Yolk antibody extraction. Egg yolk immunoglobulin (IgY) was extracted from dated eggs using a two-step polyethylene glycol 8000 (PEG 8000) process. Individual egg yolks were added to a 4.67% (w/v) PEG 8000 solution at a volumetric ratio of 1:3. Lipids and other precipitated components were removed through centrifugation at 9,000×g for 15 minutes at 4° C. The supernatant, containing solubilized immunoglobulin, was decanted and added to a 37.5% (w/v) PEG 8000 solution at a volumetric ratio of 3:1. A second centrifugation at 10,000×g for 15 minutes at 4° C. pelleted the precipitated IgY. Finally, the pellet was resuspended in sterile PBS with a volume equal to the original yolk. Purified IgY preparations were 0.2 μm sterile filtered and stored at −20° C.

ELISA Confirming Antigen Specificity

Indirect ELISA. Each of the 21 refolded sample scFv preparations were diluted 1:100 in 1% BSA.

The immunogen in its native form was immobilized in treated 96 well flat-bottom polystyrene microtiter plate wells. Once coated, the wells were blocked using 1% bovine serum albumin (BSA). To maximize the number of sample replicates, both coated antigen and sample IgY were run at a single previously optimized dilution pairing of 1:10 and 1:600, respectively. After an hour with gentle orbital shaking at room temperature, unbound IgY was removed by an automated plate washer with a three-wash configuration. A secondary antibody, a goat anti-chicken HRP conjugated antibody was added to wells and the plate was returned to the shaker for one hour at room temperature. After a four-wash removing all unbound goat antibody, a two part chromogen substrate was combined and added to all wells for 10 minutes on the benchtop. The development was stopped with 1N $H_2SO_4$ after 30 min. on the benchtop and optical density values were read at 450 nm.

Results

Few, but highly abundant reads dominated the antibody repertoire regardless of immune state. As a result of clustering by similarity, dominant CDR3 sequences for each repertoire were revealed. The clustering algorithm took several hours to cluster each repertoire; the algorithm usually ran overnight with results in the morning. A study wide analysis for the non-immune CDRH3 repertoire, including the adjuvant control, of the top four clusters in terms of abundance resulted in frequencies: 2.817% (SD=0.033), 1.556% (SD=0.017), 1.107% (SD=0.011), and 0.714% (SD=0.003). For the immunized CDRH3 repertoire, the average frequencies of the top four were: 3.087% (SD=0.023), 1.286% (SD=0.005), 1.002% (SD=0.006), and 0.784% (SD=0.002). Table 2 shows an example of one of the twelve data frames constructed from the clustering data. The data frames were constructed in Rstudio following antibody sequence clustering. Representative CDRH3 sequences for each cluster are in rows, while columns contain data regarding the clusters' repertoire copy number, frequency, and change in (delta) frequency. Only the top 10 clusters are depicted (ranked by Hyperimmunized frequency); the actual data frame has a total of 13,503 clusters.

TABLE 2

| HI Cluster | Representative CDRH3 Sequence | CDRH3 Residue Length | HI Copy Number | HI Frequency | Corresponding Non-immune Cluster | Corresponding Non-immune Copy Number | Corresponding Non-immune Frequency | Delta Frequency |
|---|---|---|---|---|---|---|---|---|
| 0 | CAKSANSGNPDAGEIDAW (SEQ ID NO: 5) | 18 | 2451 | 0.075227894 | 24 | 82 | 0.001980628 | 38.0 |
| 1 | CAKNSFSSGYGWSAGTIDAW (SEQ ID NO: 6) | 20 | 709 | 0.021761149 | 87 | 37 | 0.000893698 | 24.3 |
| 2 | CTRSSCGGDHESGCIDAW (SEQ ID NO: 7) | 18 | 701 | 0.021515607 | 14 | 115 | 0.002777711 | 7.7 |
| 3 | CARGGAGHDIDRW (SEQ ID NO: 8) | 13 | 384 | 0.01178601 | 733 | 8 | 0.000193232 | 61.0 |
| 4 | CAKTYRGGYCDNGDPCIGYRIGAW (SEQ ID NO: 9) | 24 | 342 | 0.010496915 | 1 | 453 | 0.010941765 | 1.0 |
| 5 | CVKSDDGVCCDAYGIDAW (SEQ ID NO: 10) | 18 | 238 | 0.007304871 | 2 | 303 | 0.007318664 | 1.0 |

TABLE 2-continued

| HI Cluster | Representative CDRH3 Sequence | CDRH3 Residue Length | HI Copy Number | HI Frequency | Corresponding Non-immune Cluster | Corresponding Non-immune Copy Number | Corresponding Non-immune Frequency | Delta Frequency |
|---|---|---|---|---|---|---|---|---|
| 6 | CAKGPSGYRYLVGNNIDAW (SEQ ID NO: 11) | 19 | 211 | 0.006476167 | 980 | 6 | 0.000144924 | 44.7 |
| 7 | CTRSSCGGDHEAGCIDAW (SEQ ID NO: 12) | 18 | 203 | 0.006230625 | 9 | 143 | 0.003454023 | 1.8 |
| 8 | CAKSAAGWCADAGIIDAW (SEQ ID NO: 13) | 18 | 184 | 0.005647463 | 447 | 12 | 0.000289848 | 19.5 |
| 9 | CTRSSCGGDYEAGCIDAW (SEQ ID NO: 14) | 18 | 171 | 0.005248458 | 5 | 185 | 0.004468491 | 1.2 |

Areas of conservation surround the CDR3. The CDR3 search motifs were designed and optimized using high-confidence sequence data. The search motifs successfully identified a study wide average of 92.337% (SD=3.889) of all $V_L$ sequences, and 89.791% (SD=2.322) of all $V_H$ sequences.

CDR3 lengths of the two immune states' most abundant sequences can be significantly different. Using only the top 5% of sequences within repertoire distributions, paired t-tests were performed on the lengths of CDR3, in the two immune states, for each of the five hyperimmunized chicken repertoires. After multiple test corrections using Benjamini-Hochberg controlling the FDR, two of the five immunized repertoires had CDRH3 sequences that were significantly differently sized as compared to their non-immune state repertoire (p=0.03168 each). In both cases, the 5%-selected immunized repertoire had significantly longer CDRH3s than what was observed in their non-immune 5%-selected repertoires. No chicken had significantly longer or shorter CDRL3 sequence in their two immune states. Histograms of CDR3 length distributions for one chicken that had significantly different CDRH3 lengths are in FIG. 4.

Significant antibody frequency shifts were observed between the two immune states. To compare frequency shifts in the six post-state (five immunized and one adjuvant) repertoires, 15 paired t-tests were performed. A 6×6 matrix comparing frequency shifts from a non-immune state to post-hyperimmunized repertoires in the six chickens is shown in Table 3. Yellow/Black is the adjuvant control, the other five received hyperimmunizations. Benjamini-Hocherg FDR corrected p-values from paired t-tests of Δfrequency values are shown for each pairing. Bold and underlined p-values designate significance at a confidence interval of 95% or greater. Four of the five hyperimmunized chickens had significantly greater Δfrequency values than the adjuvant control (p≤0.0474, Bonferroni corrected). Additionally, when comparing Δfrequency values within the five hyperimmunized chicken repertoires, all but one were not significantly different from one another (p≥0.1058).

TABLE 3

|  | yellow/white | green | blue | black/red | yellow | yellow/black |
|---|---|---|---|---|---|---|
| yellow/white | 1 |  |  |  |  |  |
| green | 0.9483 | 1 |  |  |  |  |
| blue | 0.1058 | 0.2351 | 1 |  |  |  |
| black/red | 0.0226 | 0.0049 | 0.0041 | 1 |  |  |
| yellow | 0.1317 | 0.0736 | 0.2486 | 0.0041 | 1 |  |
| yellow/black | 0.0113 | 0.5982 | 0.0041 | 0.0016 | 0.0005 | 1 |

Amino acid diversity in the $V_H$ region includes homologous substitutions and complements the cited literature. To evaluate amino acid diversity in the 14 paired candidate $V_L$ and $V_H$, including their derivatives, sequences were aligned to their respective IMGT germline sequences using Clustal Omega and are seen in FIG. 6. What was readily apparent were the four conserved framework (FW) regions and the three hypervariable regions (CDR). Observations seen by Wu and colleagues, a Pfizer research team in 2012 were used as a guide. Generally, comparisons with, and drawing conclusions from, CDR alignment to a germline reference are generally not productive because these are the targeted regions of VDJ recombination and gene conversion. However, some positions of residues are important and are conserved. Concerning FW1 and FW4, the complete agreement with germline was a direct result of the location of my designed amplification primers. Position 37Y, located within CDRH1, was observed by Wu and colleagues to be substituted approximately 35% of the time (n=1269) with either pairing of V/F or R/H. Position 37Y among the 14 candidates was also variable (2 instances of H and 1 instance of F). Position 39M, the leading position in FW2, was fully conserved in all candidates and has been identified as a buried structural residue. Position 40G, assigned to CDRH1 despite its physical location within FW2, was hypervariable in candidates and has been observed in mammals to interact with antigen. In FW2, position 42V was substituted for Met in six of the candidates. Together with 44Q, 50L, and 52F, the four positions have been shown to interact with the light chain variable region. Candidates were fully conserved at position 44Q, one substituted at 50L to 50A, and were variable at 52 (5 W, 1 Y, and 1 I). Wu and colleagues observed similar homologous amino acid substitutions at 52F, noting 38% of samples had Trp at position 52. Positions 53V and 54A were generally conserved in 14 candidates, with one homologous substitution at 53 for Ile and none at position 54. FW2 residues 53V and 54A have been cited in effecting CDRH2 structure, with rare deviations seen by Wu and colleagues at 1% I and 6% G, respectively. Position 55G is assigned to the CDRH2, although it is upstream of the defined hypervariable region, and was substituted for Ser in six of the 14 candidates. The C-terminal FW2 residue, 56I, was also mostly conserved with only one candidate substituting a homologous-hydrophobic valine. Similar to upstream residues, 56I effects CDRH2 structure and is a buried and conserved position in multiple species. Position 66G is another case of a residue located in a framework region, FW3, but is assigned to CDRH2 by evidence of antigen-interaction. Wu and colleagues observed hypervariability at this position and the variability can be seen in the 14 candidates (8 F/Y/W, 3 G/A, 2 R/D, 1L). A stretch of conservation runs through FW3 in all candidates, from positions 74 to 81, with no deviations from the motif 'GRATISRD'. Position 87V has been shown to be significant in maintaining affinity and Wu and colleagues observed extreme conservation at this position, with the allowed homologous substitution for Leu. This characteristic is seen in the candidate sequences, with only one candidate substituting the Val for Leu. Within the expectedly hypervariable CDRH3, there are flanking positions that appear with some frequency. At the start of CDRH3, position 104C is a site for disulfide bond formation and there is a clear CAK and CAR motif. Likewise, at the end of CDRH3, there is a general IDA or IDT motif. Overall, there are agreeable observations by the Pfizer group of Wu and colleagues, and the 14 selected candidate antigen-specific $V_H$ sequences.

DISCUSSION

Ranking CDR3 sequences based on their repertoire frequency produced animal-specific dominant antibody sequences. Non-immune (pre-HI) samples were collected from the same animal prior to hyperimmunizations. Massive clonal expansions were observed of rare or completely absent B cell clones in the non-immune state, as a result of an active humoral immune response. Quantifying the fold-change of the frequency shift between the two immune states resulted in a measurement of delta frequency (Δfrequency). Using complete immunized repertoire distributions, a comparison of Δfrequency values between non-immune (pre-HI) and hyperimmunized (post-HI) was performed as shown in Table 2.

The CD-HIT clustering algorithm (Weizhong Li et al. (Bioinformatics, 17 282-283 and Bioinformatics, 18, 77-82) was used for ranking antibody sequences by their abundance. CD-HIT uses a greedy incremental approach as well as a short word filter and index table. The algorithm first sorted sequences based on length; designating one sequence as a representative for each discrete cluster. It then attempted to find the appropriate cluster for all remaining sequences. The algorithm used a short word filter, two to five peptides, or larger, and an index table to reduce the number of time-consuming pairwise alignments. If a cluster and the query sequence exceeded a minimal threshold similarity, the sequence was added. If no clusters could overcome the threshold, the query sequence would then become the representative of a new cluster. For this study, similarity thresholds at 96%, 95%, and 90%, were set and the short word filter utilized pentapeptide similarities.

The effects of somatic hypermutation are evident in the data, in candidate antibody sequences with the creation of candidate derivatives at critical residues. These derivatives were discovered by selecting all reads containing the dominant CDR3. To infer dominant CDR1 and CDR2 within the CDR3-defined reads, the full-length $V_L$ and $V_H$ reads were submitted for a second time to CD-HIT with a similarity threshold of 96%. This threshold was chosen since the average submitted $V_L$ read length was 86.49 bp (SD=1.34, n=35,846) that allowed for no more than three mismatches. Likewise, the average $V_H$ read length was 96.33 bp (SD=2.63, n=5,911). Subclusters of clearly dominant CDR1 and CDR2 regions resulted from this analysis. The two hypervariable regions were consistently clustered together such that the most frequent CDR1 always occurred with the most frequent CDR2. This observation was confirmed with manual individual after-the-fact searches for each CDR. The subclustering of CDR1 and CDR2 by abundance within the overall CDR3-defined read seems like an effective method of monitoring somatic hypermutation.

To obtain additional understanding of the PBMC sample populations, since cells had not been enumerated or sorted prior to RNA extraction, the reoccurrence rate was calculated of the most abundant non-immune repertoire sequences in the post-state repertoires, for each of the six chickens. Abundant sequences were used comprising the top 5% of the non-immune repertoire distribution and searched their corresponding post-state repertoires. Using only the most abundant non-immune $V_L$ and $V_H$ sequences, the distribution quickly approaches zero with the dominance of singleton reads, as seen in FIGS. 6A and 6B. The reoccurrence rate for the most abundant non-immune CDRL3s in the post-state repertoires was 85.553% (SD=3.096, n=6). The CDRH3 reoccurrence rate averaged 76.265% (SD=24.101, n=6). One chicken had a very low CDRH3 recovery rate of 31.2%, bringing down the otherwise higher average of 85.278% (SD=9.668, n=5). The one chicken's low non-immune reoccurrence rate of 31.2% was the ratio of non-immune to immunized number of sequence reads. This sample had approximately 2.5:1 non-immune to immunized read count (42,833 to 17,417).

The CDRH3 sequence had more uniqueness compared to the CDRL3. Whereas there were two instances of a non-unique CDRH3, the $V_L$ CDR3 had many more non-unique sequences between the six immunized repertoires. Several CDRL3s that ended up paired with candidate CDRH3s were not unique to the chicken it originated from. Of the six chicken's $V_H$ hyperimmunized repertoires, the most abundant cluster in the adjuvant control and the $10^{th}$-ranked cluster in one hyperimmunized hen had non-exclusive hyperimmunized state CDRH3 sequences. Looking at the non-exclusive cluster from the immunized chicken, in all six cases the cluster is more abundant in the immunized repertoire than it is in the non-immune repertoire. This may be explained by similar observations seen in the adjuvant control post-state repertoire where clusters' rank commonly increased; despite no intended antigen being delivered. Because an adjuvant enhances the immune system's response to antigen, the observation of an increasing CDR3 abundance in the post-state repertoires, and not necessarily a significant shift in its ranking, might explain this result. Supporting evidence is the complementary observation that the most abundant CDRL3 in the adjuvant control was also shared amongst all other chickens. This example of paired non-exclusivity supports the robustness of rank order pairing of antibody chains. In cases where shared CDR3 sequences were identified, either they were seen at counts of less than five, or they were numerous and spread across all 12 repertoires; both immune states for the six chickens. In these ubiquitous cases, there was no bias towards either immune state.

The sequences from the 24 samples were then individually clustered, at 90% similarity, at their CDR3 regions. Twelve merged datasets were generated that contained only pre-immune sequences that were also found in the post-immune repertoire—two variable region databases for each of the six chickens. Relative population frequency changes were calculated, and along with abundance in both immune states, a custom thresholding rule was established which selected for sequences which were likely to be antigen-specific: rare or completely absent in the pre-immune repertoire, while being dominant in the post-immune repertoire. Fourteen CDRH3 sequences passed the thresholding ruleset and were paired with light chain sequences by similar relative abundance. In pairing the candidate $V_H$ sequences with their counterpart $V_L$, two pairing methods were performed and yielded very similar results. Method 1 used the CDRL3 with the closest frequency percentage to the $V_H$ candidate. Method 2 used a rank ordering such that two CDR3s would be paired despite significant differences in their repertoire frequency. Comparing the two results by a homoscedastic two tailed t-test produced no significant differences (p=0.3188). In three cases, where the most abundant $V_H$ sequences of a chickens' immunized repertoire were to be paired, the two methods used the same $V_L$ sequence. In other $V_H$ candidates that were in consecutive clusters, the difference in pairing methods was off by one CDRL3 cluster. The rank order pairing was chosen as the method of $V_H$-$V_L$ pairing as described by Reddy et al. (Nature Biotechnology, Vol. 28, p. 965-969, 2010). This resulted in success of 21-of-27 recombinantly expressed scFv s being antigen-specific.

A total of 21 candidate antigen-specific antibody sequences were identified (including different light chain pairings with the 14 heavy chains) and sequenced variable regions were spliced into scFv gene scaffolds. The scFv genes were expressed in *E. coli* BL21 (DE3) using a pET151 vector. Following solubilization of inclusion bodies and refolding, an indirect ELISA using the immunogen as antigen confirmed 16/21, or 12/14 selected candidate sequences were indeed antigen specific.

TABLE 4

| ID | scFv Sequence | Antigen Screen Results |
|---|---|---|
| CI81_1 scFv (SEQ ID NO: 15) | AVTLDESGGGLQTPGGGLSL VCKASGFTFSSYGMAWVRQA PGKGLEFVAGIAYSGSGTGY GSAVKGRATISRDNGQSTVR LQLNNLRAEDTGTYFCAKSA NSGNPDAGEIDAWGHGTEVI VSSGGGGSGGGGSGGGGSAV LAHTSGSLVQAALTEPASVS ANLGGTVKITCSGGGSSSYY GWYQQKSPGSAPVTVIYQDT ERPSNIPSRFSGSTSGSTAT LTITGVQADDEAVYFCGNED ITYVGVFGAGTTLTVL | hit |
| CI81_2 scFv (SEQ ID NO: 16) | AVTLDESGGGLQTPGGGLSL VCKASGFTFSSYDMGWVRQA PGKGLEFIAGISYSGSDTRY GSAVQGRATISRDNGQSTVR LQLNNLRAEDTGTYYCARGG AGHDIDRWGHGTEVIVSSGG GGSGGGGSGGGGSAVLAHTS GSLVQAALTEPASVSANLGG TVKITCSGSSGSYGWYQQKS PGSAPVTVIYRNDKRPSDIP SRFSGSKSGSTATLTITGVQ AEDEAVYYCGSADSSGAIFG AGTTLTVL | miss |
| CI81_3 scFv (SEQ ID NO: 17) | AVTLDESGGGLQTPGGGLSL VCKASGFTFSSYGMAWVRQA PGKGLEFVAGIAYSGSGTGY GSAVKGRATISRDNGQSTVR LQLNNLRAEDTGIYFCAKGP SGYRYLVGNNIDAWGHGTEV IVSSGGGGSGGGGSGGGGSA VLAHTSGSLVQAALTEPASV SANLGGTVKITCSGDPTYYG WYQKKSPGSAPVTLIYSNDK RPSDIPSRFSGSLSGSTNTL TITGVQVEDEAVYYCGSYDS TYDIIFGAGTTLTVL | hit |
| CI81_4 scFv (SEQ ID NO: 18) | AVTLDESGGGLQTPGGGLSL VCKASGFTFSDYGMQWVRQA PGRAGIVASISNSGSRTYYG AAVKGRATISRDDGQSTVRL QLYDLRAEDTGTYYCARTAG GCYACADDIDAWGHGTEVIV SSGGGGSGGGGSGGGGSAVL AHTSGSLVQAALTEPASVSA NLGGTVKITCSVDIIDDVTY YYGWHQQKSPGSAPVTVIYG DNQRPSDIPSRFSGSASGST ATLTITGVQADDEAVYFCGA YDSSDDVAIFGAGTTLTVL | hit |
| CI81_5 scFv (SEQ ID NO: 19) | AVTLDESGGGLQTPGGGLSL VCKASGFTFSSHGMGWVRQA PGKGLEFVASISNTGGGTAY GAAVKGRATISRDNGQSTVR LQLNNLRADDTATYYCARAP SSGYCNNVHIVDIIDTWGHG TEVIVSSGGGGSGGGGSGGG GSAVLAHTSGSLVQAALTEP ASVSANLGGTVKITCSGGSG YYGWFQQKSPGSAPVTVIYE NTKRPSDIPSRFSGSASGST ATLTITGVQVEDEAVYYCGN RDISYVAIFGAGTTLTVL | hit |
| CI81_6.1.1 scFv (SEQ ID NO: 20) | AVTLDESGGGLQTPGGGLSL VCKASGFTFSDYGMGWMRQA PGKGLEWVASVTYTGDETPF YAPAVQGRATISRDNGQSTV RLQLNSLRAEDTATYFCAKS PNSGIPNGAFIDTWGHGTEV IVSSGGGGSGGGGSGGGGSA VLAHTSGSLVQAALTEPASV SANLGGTVKITCSGSSGSYG WYQQKSPGSAPVTVIYADTK RPSDIPSRFSGSKSGSTGTL TITGVQAEDEAVYFCGGYED GTDVGIFGAGTTLTVL | hit |
| CI81_6.1.2 scFv (SEQ ID NO: 21) | AVTLDESGGGLQTPGGGLSL VCKASGFTFSDYGMGWMRQA PGKGLEWVASVTYTGDETPF YAPAVQGRATISRDNGQSTV RLQLNSLRAEDTATYFCAKS PNSGIPNGAFIDTWGHGTEV IVSSGGGGSGGGGSGGGGSA VLAHTSGSLVQAALTEPASV SANLGGTVKITCSGSSGSYG | hit |

TABLE 4-continued

| ID | scFv Sequence | Antigen Screen Results |
|---|---|---|
| | WYQQKSPGSAPVTVIYADTKRPSDIPSRFSGSTSGSTGTLTITGVQAEDEAVYFCGGYEDGTDVGIFGAGTTLTVL | |
| CI81_6.1.3 scFv (SEQ ID NO: 22) | AVTLDESGGGLQTPGGGLSLVCKASGFTFSDYGMGWMRQAPGKGLEWVASVTYTGDETPFYAPAVQGRATISRDNGQSTVRLQLNSLRAEDTATYFCAKSPNSGIPNGAFIDTWGHGTEVIVSSGGGGSGGGGSGGGGSAVLAHTSGSLVQAALTEPASVSANLGGTVKITCSGSSGSYGWYQQKSPGSAPVTVIYADTKRPSDIPSRFSGSTSDSTGTLTITGVQAEDEAVYFCGGYEDGTDVGIFGAGTTLTVL | miss |
| CI81_6.2.1 scFv (SEQ ID NO: 23) | AVTLDESGGGLQTPGGGLSLVCKASGFTFSDYGMGWMRQAPGKGLEWVASVTYTGDETPFYAPAVQGRATISRDNGQSTVRLQLNSLRAEDTATYFCAKSPNSGIPNGAFIDTWGHGTEVIVSSGGGGSGGGGSGGGGSAVLAHTSGSLVQAALTEPASVSANLGGTVKITCSGSSGSYGWYQQKSPGSAPVTVIYANTNRPSDIPSRFSGSKSGSTATLTITGVQAEDEAVYFCGGYEDGTDVGIFGAGTTLTVL | hit |
| CI81_6.2.2 scFv (SEQ ID NO: 24) | AVTLDESGGGLQTPGGGLSLVCKASGFTFSDYGMGWMRQAPGKGLEWVASVTYTGDETPFYAPAVQGRATISRDNGQSTVRLQLNSLRAEDTATYFCAKSPNSGIPNGAFIDTWGHGTEVIVSSGGGGSGGGGSGGGGSAVLAHTSGSLVQAALTEPASVSANLGGTVKITCSGSSGSYGWYQQKSPGSAPVTVIYANTNRPSDIPSRFSGSPSGSTATLTITGVQAEDEAVYFCGGYEDGTDVGIFGAGTTLTVL | miss |
| CI81_7.1 scFv (SEQ ID NO: 25) | AVTLDESGGGLQTPGGGLSLVCKASGFTFSDYGMGWMRQAPGKGLEWVAGISSSGSDTYYGAAVKGRATISRDNGQSTVRLQLNNLRTEDTATYFCAKSANNMCDNTGCAAGQIDTWGHGTEVIVSSGGGGSGGGGSGGGGSAVLAHTSGSLVQAALTEPASVSANLGGTVKITCSGSGRYGWYQQKSPGSAPVTVIYADTNRPSDIPSRFSGSKSGSTATLTITGVQADDEAVYYCGNYEGGFFNDIFGAGTTLTVL | hit |
| CI81_7.2 scFv (SEQ ID NO: 26) | AVTLDESGGGLQTPGGGLSLVCKASGFTFSDYGMGWMRQAPGKGLEWVAGIGSTGSSTYYGAAVKGRATISRDNGQSTVRLQLNNLRTEDTATYFCAKSANNMCDNTGCAAGQIDTWGHGTEVIVSSGGGGSGGGGSGGGGSAVLAHTSGSLVQAALTEPASVSANLGGTVKITCSGSGRYGWYQQKSPGSAPVTVIYADTNRPSDIPSRFSGSKSGSTATLTITGVQADDEAVYYCGNYEGGFFNDIFGAGTTLTVL | hit |
| CI81_8.1 scFv (SEQ ID NO: 27) | AVTLDESGGGLQTPGGGLSLVCKASGFTFSSHGMGWVRQAPGKGLEYVASITSIDDGETPFYAPAVQGRATISRDDGQSTVRLQLNNLRAEDTGTYYCTKSPNSGIPNGAFIDTWGHGTEVIVSSGGGGSGGGGSGGGGSAVLAHTSGSLVQAALTEPASVSANLGGTVKITCSGGGNNYGWHQQKSPGSAPVTVIYSNDKRPSDIPSRFSGSASGSTGTLTITGVQAEDEAVYFCGGYDGNNGAFGAGTTLTVL | miss |
| CI81_8.2 scFv (SEQ ID NO: 28) | AVTLDESGGGLQTPGGGLSLVCKASGFTFSSHGMGWVRQAPGKGLEYVASITSIDDGETPFYAPAVQGRATISRDDGQSTVRLQLNNLRAEDTGTYYCTKSPNSGIPNGAFIDTWGHGTEVIVSSGGGGSGGGGSGGGGSAVLAHTSGSLVQAALTEPASVSANLGGTVKITCSGGGNNYGWHQQKSPGSAPVTVIYSSDKRPSDIPSRFSGSASGSTGTLTITGVQVEDEAVYFCGGYDGNNGAFGAGTTLTVL | hit |
| CI81_8.3 scFv (SEQ ID NO: 29) | AVTLDESGGGLQTPGGGLSLVCKASGFTFSSHGMGWVRQAPGKGLEYVASITSIDDGETPFYAPAVQGRATISRDDGQSTVRLQLNNLRAEDTGTYYCTKSPNSGIPNGAFIDTWGHGTEVIVSSGGGGSGGGGSGGGGSAVLAHTSGSLVQAALTEPASVSANLGGTVKITCSGGGNNYGWHQQKSPGSAPVTVIYSTDKRPSDIPSRFSGSASGSTATLTITGVQVEDEAVYFCGGYDGNNGAFGAGTTLTVL | hit |
| CI81_9 scFv (SEQ ID NO: 30) | AVTLDESGGGLQTPGGGLSLVCKASGFTFNDYGMGWMRQAPGKGLEFVASITSATDNETPFYAPAVQGRATISRDNGQSTVRLQLNNLRAEDTATYYCAKSPNSGIPNGAFTDTWGHGTEVIVSSGGGGSGGGGSGGGGSAVLAHTSGSLVQAALTEPASVSANLGGTVKITCSGSRGSYGWYQQKSPGSAPVTVIYSNDKRPSDIPSRFSGSRSGSTATLIITGVRAEDEAVYFCGSYEGGFFNDIFGAGTTLTVL | hit |
| CI81_10 scFv (SEQ ID NO: 31) | AVTLDESGGGLQTPGGGLSLVCKASGFNFSDYNMGWVRQAPGKGLEWVAGIYSGYDTYYATAVDGRATISRDDGQTTVRLQLDDLRAEDTGTYFCTRGAAPYYIDTWGHGTEVIVSSGGGGSGGGGSGGGGSAVLAHTSGSLVQAALTEPASVSANLGGTVKITCSGSSGSYGWYQQKSPGSAPVTVIYADTKRPSDIPSRFSGSTSGSTSTLTITGVQAEDEAVYFCGGYEDGIDVGIFGAGTTLTVL | hit |
| CI81_11 scFv (SEQ ID NO: 32) | AVTLDESGGGLQTPGGGLSLVCKASGFTFSSYAMGWMRQAPGKGLEFVAGIRGDGSSTWYATAVQGHATISRDDGQSTLRLQLNNLRAEDTATYFCAKNG | hit |

TABLE 4-continued

| ID | scFv Sequence | Antigen Screen Results |
|---|---|---|
|  | YDGNRWGAYSADSIDAWGHG TEVIVSSGGGGSGGGGSGGG GSAVLAHTSGSLVQAALTEP ASVSANLGGTVKITCSGSSG SYGWYQQKSPGSAPVTVIYA DTKRPSDIPSRFSGSTSGST STLTITGVQAEDEAVYFCGG YEDGIDVGIFGAGTTLTVL |  |
| CI81_12 scFv (SEQ ID NO: 33) | AVTLDESGGGLQTPGGGLSL VCKASGFTFSDYGMGWMRQA PGKGLEFVASITSSIDNETP FYAPAVQGRATISRDDGQST VRLQLNDLRAEDTGTYYCAK SPNSGIPNGAFTETWGHGTE VIVSSGGGGSGGGGSGGGS AVLAHTSGSLVQAALTEPAS VSANLGGTVKITCSGGGGSY YGWYQQKSPGSAPVTVIYSN NKRPSDIPSRFSGALSGSTV TLTITGVQAEDEAVYYCGSY DSSGGIFGAGTTLTVL | hit |
| CI81_13 scFv (SEQ ID NO: 34) | AVTLDESGGGLQTPGGGLSL VCKASGFTFSSFNMMWVRQA PGKSLEWVAGIQNIGSGTDY GAAVKGRATISRDNGQSTVR LQLNNLRAEDTGTYYCARGA GGCASCADDIDAWGHGTEVI VSSGGGGSGGGGSGGGGSAV LAHTSGSLVQAALTEPASVS ANLGGTVKITCSGGGGSYYG WYQQKSPGSAPVTVIYSNNK RPSDIPSRFSGALSGSTVTL TITGVQAEDEAVYYCGSYDS SGGIFGAGTTLTVL | hit |
| CI81_14 scFv (SEQ ID NO: 35) | AVTLDESGGGLQTPGGGLSL VCKASGFTFSSYTMNWVRQA PGKGLEWVAGINNFGNTTLR VAVKGRATISRDNGQTTVRL QLNNLRAEDTATYFCAKNAA GSCINCADNIDVWGHGTEVI VSSGGGGSGGGGSGGGGSAV LAHTSGSLVQAALTEPASVS ANLGGTVKITCSGSTYNYGW YQQKSPGSAPVTVIYYNDKR PSGIPSRFSGSKSGSTGTLT ITGVRAEDEAIYYCAGYDSN AGIFGAGTTLTVL | miss |

Example 2

Transient Expression in *E. coli* and ELISA Confirming Antigen Specificity

Vials of chemically-competent *E. coli* BL21 Star™(DE3) from Invitrogen were thawed on ice for a minimum of one hour. Plasmid was received from Invitrogen's GeneArt Gene Synthesis service in the form of a 5 ug lyophilized pellet. That pellet was suspended in 50 uL nuclease-free water; creating a DNA concentration of 100 ng/uL. The plasmid preparations at a concentration of 100 ng/uL were then further diluted, using nuclease-free water, to a concentration of 5 ng/uL. Once the *E. coli* cells had thawed, 2 uL of the 5 ng/uL diluted plasmid was added to the vial and gently mixed by flicking. Following a 30 minute incubation on ice, allowing salts in the plasmid preparation to stabilize cell membranes, a precise 30 second heat-shock at 42° C. drove plasmids into cells. Vials were immediately returned to the ice bath. Next, 250 uL of S.O.C. media (kit provided) was added to vials which allowed cells to recover and began expressing the antibiotic resistance gene. Vials were incubated with shaking at 37° C. After 30 minutes, vials were used to inoculate 10 mL test tubes containing Luria-Bertani (LB) broth with 50 ug/mL carbenicillin antibiotic. Cultures were incubated overnight at 37° C. with shaking. The next morning, culture volumes were scaled up by inoculating 5% (v/v) 250 mL Erlenmeyer flasks with 80 mL LB broth supplemented with 50 ug/mL carbenicillin. Pre-warming the 80 mL media ensured a faster transition to logarithmic growth phase. Cultures were incubated at 37° C. 200 RPM for 2 hours and 45 minutes.

Once in logarithmic growth phase, expression of the scFv protein was induced by adding IPTG to a final culture concentration of 0.8 mM. IPTG was slowly pipetted into flasks with constant shaking and returned to 37° C. 200 RPM for 4 hours. To harvest recombinant protein, cultures were centrifuged to pellet *E. coli* for 10 minutes at 4,000×g at 4° C. Spent culture media was discarded and cell pellets were stored by inverting centrifuge tubes at −80° C. To collect the expressed scFvs, *E. coli* pellets were pulled from −80° C. storage and cells were fully lysed using Novagen's Bug-Buster Lysis Buffer at 20% (v/v) of the culture volume. Since centrifuge tubes held approximately 40 mL, 5 mL of Lysis Buffer was added and cells were lysed by gently rocking on the benchtop for 20 minutes. Next, centrifuging tubes for 20 minutes at 16,000×g 4° C. separated soluble (supernatant) and insoluble (pellet) protein. Both protein fractions were collected for analysis.

As determined by SDS-PAGE and evaluating protein bands, the recombinant scFv was found to be in the insoluble protein fraction; specifically in aggregates called inclusion bodies. Following failed attempts at histidine tag purifications, all 21 expressed scFvs were determined to be misfolded and required re-solubilization and subsequent refolding to restore proper folding and activity. The 21 scFv inclusion body preparations were further treated with Novagen's BugBuster Lysis Buffer; 20% (v/v) of the culture volume and the addition of lysozyme to a final concentration of 1000 U/mL. Preparations were rocked at 5 minutes on the benchtop to degrade membranes and release inclusion bodies. Another addition of Lysis Buffer, this time an equal volume of 1:10 diluted in nuclease-free water, was followed by maximum vortexing for 1 minute. Fully homogenized sample preparations were then centrifuged at 5,000×g for 15 minutes at 4° C. to pellet inclusion bodies. Supernatants were discarded.

Inclusion bodies were next washed three times in an equal volume of 1:10 diluted Lysis Buffer and collected each time through centrifugation at the same speed, time and temperature. After sample inclusion bodies of recombinant scFv were purified from *E. coli* lysates, they were re-solubilized using Thermo Scientific's Inclusion Body Solubilization Reagent. Supplemented with 5 mM DTT for reconstructing disulfide bonds, 4 mL was added to each tube and inclusion bodies were homogenized by rocking on the benchtop for 30 minutes. A final centrifugation at 27,000×g for 15 minutes separated unwanted debris. Approximately 4 mL of supernatant, containing the scFvs, were then loaded into 10,000 MWCO G2 dialysis cassettes (Thermo Scientific). A maximum of 4 cassettes at a time were dialyzed against 2L of 6M Urea at 4° C. Urea was stirred using a magnetic stir bar on a stir plate to maximize diffusion.

Recombinant scFvs were fully denatured for 6 hours before the stepwise addition of 8 portions of 250 mL 25 mM Tris-HCl, pH 7.5 every 6 or 12 hours, until the dialysis volume reached 3 L. The slow titration of tris buffer optimizes protein refolding. To remove traces of Urea, cassettes were transferred to 1 L of 25 mM Tris-HCl 150 mM NaCl pH 7.5, and dialyzed at 4° C. for 6 hours. Sample scFvs were finally collected from cassettes by needle and syringe, aliquoted into 500 uL volumes in microcentrifuge tubes, and stored at both 4° C. and −20° C.

Figure 7:
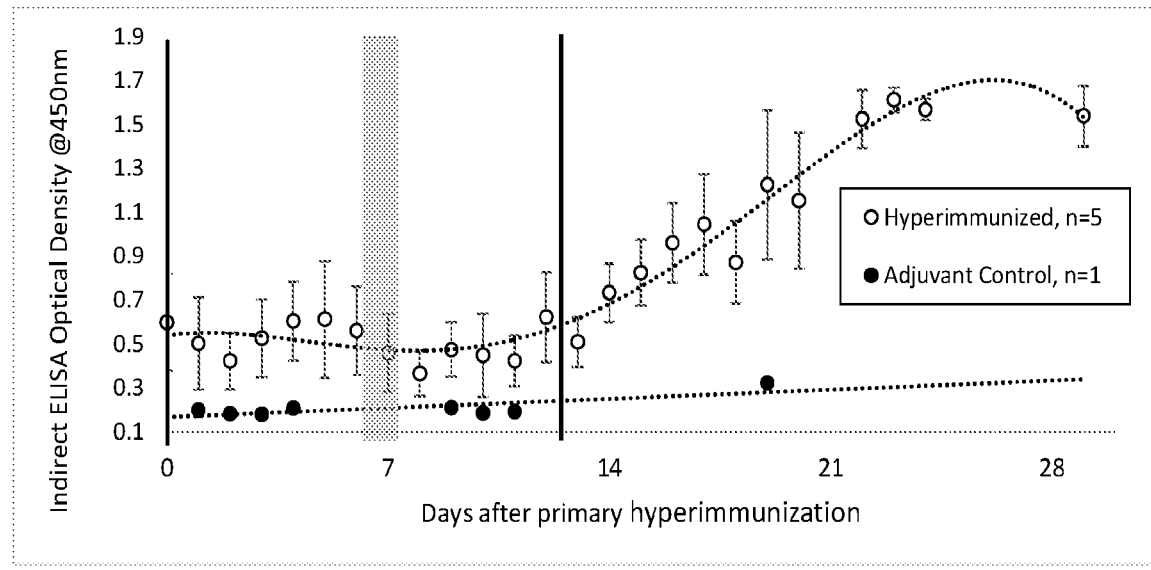
FIG. 7 is a plot of immune response curves of ELISA from dated eggs validating a successful hyperimmunization. The vertical black lines designate blood collection time points. The gray shaded region represents the 5 to 6 day delay in the hyperimmunized samples, seen in immunoglobulins from egg yolks as compared to circulating IgG. The black dashed line fitting the Hyperimmunized (white circles) was used to visualize trends only and has no statistical significance.

The ELISA immune response curves, seen in FIG. 7, support the hyperimmunized blood collection time point at six days after the boost. In FIG. 7, the immune response curves of ELISA from dated eggs validate a successful hyperimmunization. The vertical black lines designate blood collection time points. The gray shaded region represents the 5 to 6 day delay in the hyperimmunized samples, seen in immunoglobulins from egg yolks as compared to circulating IgG. The black dashed line fitting the Hyperimmunized (white circles) was used to visualize trends only and has no statistical significance.

Timing the ASC migration from the germinal centers in lymph nodes to the bone marrow can be visualized by the response curve specific to IgG/IgY. The delay seen in egg yolk-derived IgY; IgY levels are representative of the circulating immunoglobulins approximately five to six days previously. Taking this delay into account, the ELISA further supports the post-state sampling time point of six days following the boost.

Figure 9:
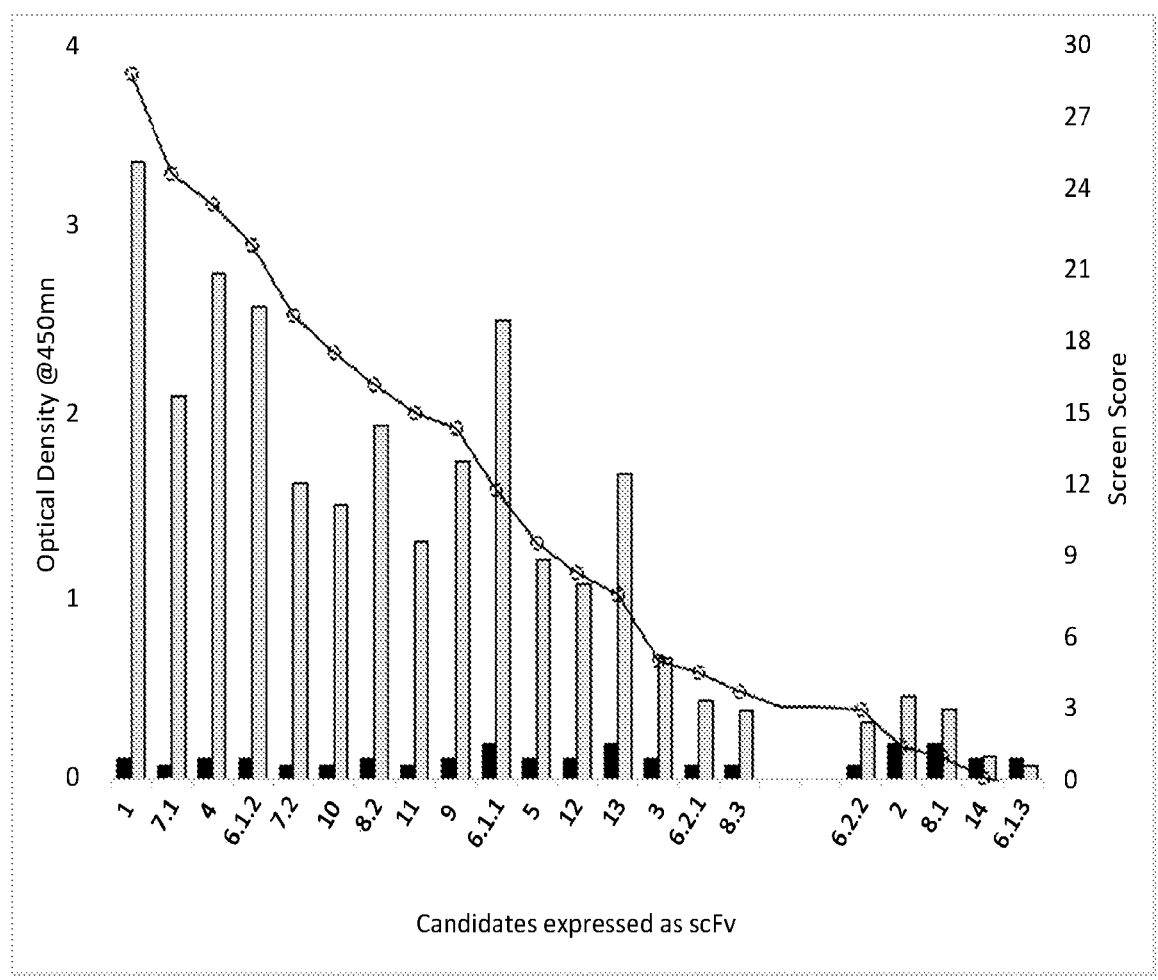
FIG. 9 is a plot of antigen specificity ELISA data of the 21 expressed candidate scFvs-16 hits and 5 misses.

FIG. 9 shows the antigen specificity ELISA data of the 21 expressed candidate scFvs-16 hits and 5 misses. The direct ELISA had immunogen coated and wells blocked with 1% BSA. Sample binding was detected using a commercial anti-chicken HRP IgG. Sample binding was detected using a commercial anti-chicken HRP IgG. Screen score (white points with black line) was determined by dividing the sample signal (gray) by the background with no sample (black). A positive result required signal greater than three times above background.

This demonstrated the ability to sequence individual chickens' antibody repertoires at two immunological time points where major frequency shifts as a result of hyperimmunization could be observed. The sample richness of peripheral blood compared to bone marrow pales in comparison, but sampling bone marrow mandates a singular sampling time point.

Unselected and unsorted cells were used. Antibody light and heavy chain mRNA transcripts being targeted by the amplifying primers are not known to be antigen-experienced, or even the secreted form of the BCR. To have selected for only secreted forms of the BCR, the heavy chain reverse primer would have to be positioned further downstream into the $C_H4$ region, where numerous hydrophilic residues reside. This would be impractical however, since moving the primer downstream would create an amplicon exceeding current Ion Torrent sequence read length limits. An additional consideration of this approach is that naïve B cells can contribute transcripts to the repertoire alongside an antigen-experienced ASC. An improvement effecting sequencing read quality can allow for additional reads to be included, a possible solution might be in multiple and redundant amplification primers, or using 5' RACE (rapid amplification of cDNA ends).

Although the present invention has been described with reference to preferred embodiments, workers skilled in the art will recognize that changes may be made in form and detail without departing from the spirit and scope of the invention.

What is claimed is:

1. A method for identifying and expressing binding domains for an antigen comprising:
    isolating nucleic acids from peripheral blood mononuclear cells of birds from samples collected prior to hyperimmunization and after hyperimmunization;
    reverse transcribing the mRNA in the samples after enriching the samples for mRNA;
    amplifying the variable regions of the heavy chains and light chains of the immunoglobulin genes using primers;
    sequencing across the majority of light and heavy chain variable regions of the immunoglobulins;
    identifying variable heavy chain amino acid sequences and the abundance of the variable heavy chain amino acid sequences;
    identifying variable light chain amino acid sequences that are approximately similar in abundance to the most abundant variable heavy chain amino acid sequences; and
    expressing polypeptides comprising the identified variable heavy chain amino acid sequences and the identified variable light chain amino acid sequences in an in vitro expression system, wherein the binding domains comprise the variable heavy chain and the variable light chain amino acid sequences, wherein the binding domains comprise scFv polypeptides, and wherein the scFv polypeptides are selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34 and SEQ ID NO:35.

2. The method of claim 1 wherein the antigen comprises *Mannheimia haemolytica* outer membrane protein (Omp) and/or *M. haemolytica* leukotoxin.

3. The method of claim 1 wherein the binding domains are in a rmAb.

4. The method of claim 1 further comprising administering a composition comprising the recombinant polypeptides expressed in the in vitro expression system having the binding domains capable of binding the antigen, wherein the binding domain of the recombinant polypeptide comprises the identified variable heavy chain amino acid sequences and the identified variable light chain amino acid sequences from the antibody repertoire of the birds hyperimmunized with the antigen, wherein the antigen is a disease related antigen and wherein administration of the composition prevents the disease in an animal.

5. The method of claim 4, wherein the recombinant polypeptides are expressed in a bacterial expression system.

6. The method of claim 4, wherein the birds are chickens.

7. The method of claim 4, wherein the antigen is *Mannheimia haemolytica* outer membrane protein (Omp) and/or *M. haemolytica* leukotoxin.

8. The method of claim 4 wherein the disease is bovine respiratory disease.

9. The method of claim 4, wherein the recombinant polypeptide is a scFv polypeptide.

10. The method of claim 4, wherein the recombinant polypeptide is a rmAb.

11. The method of claim 1, wherein the variable heavy chain amino acid sequences are complementary determining region 3 of heavy chains (CDRH3) and the variable light chain amino acid sequences are complementary determining region 3 of light chains (CDRL3).

12. The method of claim 1, wherein the identifying the abundance of the variable heavy chain amino acid sequences comprises identifying about 3 to about 6 of the most abundant variable heavy chain amino acid sequences.

13. A method for identifying and expressing binding domains for an antigen comprising:
    isolating nucleic acids from peripheral blood mononuclear cells of birds from samples collected prior to hyperimmunization and after hyperimmunization;
    reverse transcribing the mRNA in the samples after enriching the samples for mRNA;
    amplifying the variable regions of the heavy chains and light chains of the immunoglobulin genes using primers;
    sequencing across the majority of light and heavy chain variable regions of the immunoglobulins;
    identifying variable heavy chain amino acid sequences and variable light chain amino acid sequences; and
    expressing polypeptides comprising the identified variable heavy chain amino acid sequences and variable light chain amino acid sequences in an in vitro expression system, wherein the binding-domains comprise the variable heavy chain and the variable light chain amino acid sequences, the binding domains comprise scFv polypeptides, wherein the scFv polypeptides are selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34 and-SEQ ID NO:35.

14. The method of claim 13, wherein the antigen comprises *Mannheimia haemolytica* outer membrane protein (Omp) and/or *M. haemolytica* leukotoxin.

15. The method of claim 13, wherein the variable heavy chain amino acid sequences are complementary determining region 3 of heavy chains (CDRH3) and the variable light chain amino acid sequences are complementary determining region 3 of light chains (CDRL3).

16. The method of claim 13, further comprising administering a composition comprising the recombinant polypeptides expressed in the in vitro expression system having the binding domains capable of binding the antigen, wherein the binding domain of the recombinant polypeptide comprises the identified variable heavy chain amino acid sequences and the identified variable light chain amino acid sequences from the antibody repertoire of the birds hyperimmunized with the antigen, wherein the antigen is a disease related antigen and wherein administration of the composition prevents the disease in an animal.

17. The method of claim 16, wherein the recombinant polypeptides are expressed in a bacterial expression system.

18. The method of claim 16, wherein the birds are chickens.

19. The method of claim 16, wherein the disease is bovine respiratory disease.

\* \* \* \* \*